(12) United States Patent
Schafer et al.

(10) Patent No.: US 11,759,661 B2
(45) Date of Patent: Sep. 19, 2023

(54) ULTRASONIC TRANSDUCER TREATMENT DEVICE

(71) Applicant: BRAINSONIX CORPORATION, Sherman Oaks, CA (US)

(72) Inventors: Mark Evan Schafer, Ambler, PA (US); Alexander Bystritsky, Sherman Oaks, CA (US); Christopher H. Scholl, West Chester, PA (US); Joseph Jackson, Wilmington, DE (US)

(73) Assignee: BRAINSONIX CORPORATION, Sherman Oaks, CA (US)

( * ) Notice: Subject to any disclaimer, the term of this patent is extended or adjusted under 35 U.S.C. 154(b) by 288 days.

(21) Appl. No.: 16/879,649

(22) Filed: May 20, 2020

(65) Prior Publication Data

US 2021/0361975 A1 Nov. 25, 2021

(51) Int. Cl.
*A61N 7/00* (2006.01)
(52) U.S. Cl.
CPC ........ *A61N 7/00* (2013.01); *A61N 2007/0026* (2013.01); *A61N 2007/0091* (2013.01)
(58) Field of Classification Search
CPC .............. A61N 7/00; A61N 2007/0026; A61N 2007/0091
See application file for complete search history.

(56) References Cited

U.S. PATENT DOCUMENTS

| 4,343,301 | A | 8/1982 | Indech |
|---|---|---|---|
| 5,247,935 | A | 9/1993 | Cline |
| 5,275,165 | A | 1/1994 | Ettinger |
| 5,282,593 | A | 2/1994 | Fast |
| 5,291,890 | A | 3/1994 | Cline |
| 5,323,779 | A | 6/1994 | Hardy |

(Continued)

FOREIGN PATENT DOCUMENTS

| EP | 3554636 A1 | 10/2019 |
|---|---|---|
| JP | 2020-501734 | 1/2020 |

(Continued)

OTHER PUBLICATIONS

Yoo, et al., Focused ultrasound modulates region-specific brain activity, Elsevier Journal-NeuroImage, vol. 56, 2011, pp. 1267-1275.

(Continued)

*Primary Examiner* — Hien N Nguyen
(74) *Attorney, Agent, or Firm* — Schwabe, Williamson & Wyatt, PC

(57) ABSTRACT

Embodiments herein provide an ultrasonic treatment device that includes a transducer holder to hold an ultrasonic transducer. The transducer holder includes multiple mounting positions for the ultrasonic transducer to enable the transducer to be held by the transducer holder at different angles. For example, in some embodiments, the transducer holder may include multiple mounting elements on an interior surface of the transducer holder. The mounting elements may be, for example, ridges or grooves on the interior surface. The transducer may include and/or be provided with one or more locking elements that interact with the mounting elements of the transducer holder to hold the transducer within the transducer holder. Other embodiments may be described and claimed.

19 Claims, 19 Drawing Sheets

(56) References Cited

U.S. PATENT DOCUMENTS

| | | |
|---|---|---|
| 5,381,794 A | 1/1995 | Tei |
| 5,409,446 A | 4/1995 | Rattner |
| 5,546,438 A | 8/1996 | Hynecek |
| 5,738,625 A | 4/1998 | Gluck |
| 5,752,515 A | 5/1998 | Jolesz |
| 6,066,123 A | 5/2000 | Li |
| 6,088,613 A | 7/2000 | Unger |
| 6,094,598 A | 7/2000 | Elsberry |
| 6,148,225 A | 11/2000 | Kestler |
| 6,198,956 B1 | 3/2001 | Dunne |
| 6,198,958 B1 | 3/2001 | Ives |
| 6,261,231 B1 | 7/2001 | Damphousse |
| 6,267,734 B1 | 7/2001 | Ishibashi |
| 6,348,793 B1 | 2/2002 | Balloni |
| 6,413,216 B1 | 7/2002 | Cain |
| 6,612,988 B2 | 9/2003 | Maor |
| 6,708,051 B1 | 3/2004 | Durousseau |
| 7,283,861 B2 | 10/2007 | Bystritsky |
| 7,300,414 B1 | 11/2007 | Holland |
| 7,427,265 B1 | 9/2008 | Keilman |
| 7,450,985 B2 | 11/2008 | Meloy |
| 7,505,807 B1 | 3/2009 | Kucharczyk |
| 7,896,821 B1 | 3/2011 | Magnin |
| 8,086,296 B2 | 12/2011 | Bystritsky |
| 8,343,083 B1 | 1/2013 | Fencel |
| 9,061,133 B2 | 6/2015 | Wurster |
| 9,630,029 B2 | 4/2017 | Wurster |
| 10,265,497 B2 | 4/2019 | Tsai |
| 10,512,794 B2 | 12/2019 | Wurster |
| 10,792,519 B2 | 10/2020 | Wurster |
| 10,974,078 B2 | 4/2021 | Jordan |
| 2002/0042121 A1 | 4/2002 | Riesner |
| 2002/0103436 A1 | 8/2002 | Njenanze |
| 2002/0127230 A1 | 9/2002 | Chen |
| 2002/0173697 A1 | 11/2002 | Lenhardt |
| 2003/0204135 A1 | 10/2003 | Bystritsky |
| 2004/0048795 A1 | 3/2004 | Ivanova |
| 2005/0020945 A1 | 1/2005 | Tosaya |
| 2005/0240126 A1 | 10/2005 | Roley |
| 2006/0184069 A1 | 8/2006 | Vaitekunas |
| 2007/0016031 A1 | 1/2007 | Mourad |
| 2007/0299370 A1 | 12/2007 | Bystritsky |
| 2008/0262350 A1 | 10/2008 | Unger |
| 2008/0275340 A1 | 11/2008 | Beach |
| 2009/0005711 A1 | 1/2009 | Konofagou |
| 2009/0112133 A1 | 4/2009 | Deisseroth |
| 2009/0254154 A1 | 10/2009 | De Taboada |
| 2010/0010394 A1 | 1/2010 | Liu |
| 2011/0092800 A1 | 4/2011 | Yoo |
| 2011/0094288 A1 | 4/2011 | Medan |
| 2011/0166444 A1* | 7/2011 | Elgort ............... A61B 17/064 600/424 |
| 2011/0172653 A1 | 7/2011 | Schneider |
| 2011/0213200 A1 | 9/2011 | Mishelevich |
| 2011/0264012 A1 | 10/2011 | Lautzenhiser |
| 2012/0060847 A1 | 3/2012 | Stratton |
| 2012/0083719 A1 | 4/2012 | Mishelevich |
| 2014/0058293 A1 | 2/2014 | Hynynen et al. |
| 2014/0074181 A1 | 3/2014 | Slutsky |
| 2014/0186423 A1 | 7/2014 | Gelfand |
| 2014/0188011 A1 | 7/2014 | Wurster |
| 2015/0297176 A1 | 10/2015 | Rincker |
| 2016/0067526 A1 | 3/2016 | Yang |
| 2017/0105700 A1 | 4/2017 | Bar-Zion |
| 2017/0182339 A1 | 6/2017 | Wurster |
| 2018/0117364 A1 | 5/2018 | Jordan |
| 2018/0304101 A1 | 10/2018 | Yang |
| 2019/0021666 A1* | 1/2019 | Hynynen ............... A61B 8/42 |
| 2020/0121958 A1 | 4/2020 | Wurster |
| 2020/0123681 A1 | 9/2020 | Zuk |

FOREIGN PATENT DOCUMENTS

| | | |
|---|---|---|
| WO | 2017/195309 A1 | 11/2017 |
| WO | 2018/112269 A1 | 6/2018 |

OTHER PUBLICATIONS

Mulgaonkar et al., A prototype stimulator system for noninvasive low intensity focused ultrasound delivery; Stud Health Technol Inform, vol. 173, 2012, pp. 297-303.

Min et al, Focused ultrasound-mediated suppression of chemically-induced acute epileptic EEG activity, BMC Neuroscience; 2011, 12:23, pp. 1-12.

Bystritsky et al., "A review of low-intensity focused ultrasound pulsation", Elsevier Journal—Brain Stimulation, vol. 4, 2011, pp. 125-136.

Barlow, et al., The risk of seizure after receipt of whole-cell pertussis or measles, mumps, and rubella vaccine, New England journal of Medicine, vol. 345, No. 9, pp. 656-661 (2001).

Tyler, et al., Remote excitation of neuronal circuits using low-intensity, low-frequency ultrasound, PlosOne, vol. 3, Issue 10, pp. 1-11 (Oct. 2008).

Turfail, et al., Ultrasonic neuromodulation by brain stimulation with transcranial ultrasound, Nature Protocols, vol. 6, No. 9, pp. 1453-1470 (2011).

Clement et al., A hemisphere array for non-invasive brain therapy and surgery, Physics in Medicine and Biology, vol. 45, No. 12, pp. 3707-3719 (2000).

Colucci et al., Focused ultrasound effects on nerve action potential in vitro, Ultrasound in Med. & Biol., vol. 35, No. 10, pp. 1737-1747 (2009).

Tufail, et al., Transcranial Pulsed Ultrasound Stimulates Intact Brain Circuits, Neuron, vol. 66, pp. 681-694 (Jun. 10, 2010).

Yang, et al., Transcranial focused ultrasound to the thalamus is associated with reduced extracellular GABA levels in rats, Neruopsychobiology, vol. 65, pp. 153-160 (2012).

Yoo, et al., Transcranial focused ultrasound to the thalamus alters anesthesia time in rats, Neuroreport, vol. 22(15), pp. 783-787 (Oct. 26, 2011).

Hameroff, et al., Transcranial ultrasound (TUS) effects on mental states: a pilot study, Brain Stimulation, vol. 6, pp. 409-415 (2013).

Korb, et al., Low-intensity focused ultrasound pulsation device used during magnetic resonance imaging: evaluation of magnetic resonance image-related heating at 3 tesla/128MHz, Neuromodulation, (2013).

Bystritsky et al., A preliminary study of fMRI-guided rTMS in the treatment of generalized anxiety disorder, J Clin Psychiatry, vol. 69, pp. 1092-1098 (Jul. 7, 2008).

Deffieux et al., Low-intensity focused ultrasound modulates monkey visuomotor behavior, Current Biology, vol. 23, pp. 2430-2433 (Dec. 2, 2013).

Mehic et al., Increased anatomical specificity of neuromodulation via modulated focused ultrasound, Plos One, vol. 9, Issue 2, pp. 1-13 (Feb. 2014).

Kim et al., Estimation of the spatial profile of neuromodulaton and the temporal latency in motor responses induced by focused ultrasound brain stimulation, Neurophysiology Neuroreport, vol. 25, No. 7., pp. 475-479 (2014).

Metwally, et al., Influence of the antisotropic mechanical properties of the skull in low-intensity focused ultrasound towards neuromodulation of the brain, 35th Ann Int Conf of IEEE EMBS, Osaka, Japan pp. 4565-4568 (Jul. 3-7, 2013).

Winhye, et al., Creation on various skin sensations using pulsed focused ultrasound: evidence for functional neuromodulation, International Journal of Imaging Sytems and Technology, (Dec. 27, 2013).

Tyler et al., Remote excitation of neuronal circuits using low intensity, low frequency ultrasound, Ultrasonic Neurostimulation, vol. 3, No. 10, pp. 1-11 (2008).

Tyler, W.J., Noninvasive Neuromodulation with Ultrasound? A continuum mechanics hypothesis, pp. 1-12 (2010).

(56) References Cited

OTHER PUBLICATIONS

Jordao, JF et al., "Amyloid-beta plaque reduction, endogenous antibody delivery and glial activation by brain-targeted, transcranial focused ultrasound," Exp Neurol. Oct. 2013; 248: 16-29. Published online May 21, 2013; retrieved from the Internet <https://www.sciencedirect.com/science/article/pll/S00144886130 01544?via%3Dihub> <doi: 10.1016/j.expneurol.2013.5.008>.

Leinenga, G., et al. "Scanning ultrasound removed amyloid-beta and restores memory in an Alzheimer's disease mouse model," Scie Transl Med.; Mar. 11, 2015; 7 (278):278ra33. Retrieved from the Internet <http://stm.sciencemag.org/content/7/278/278ra33> <doi:10.1126/scitranslmed.aaa2512>.

* cited by examiner

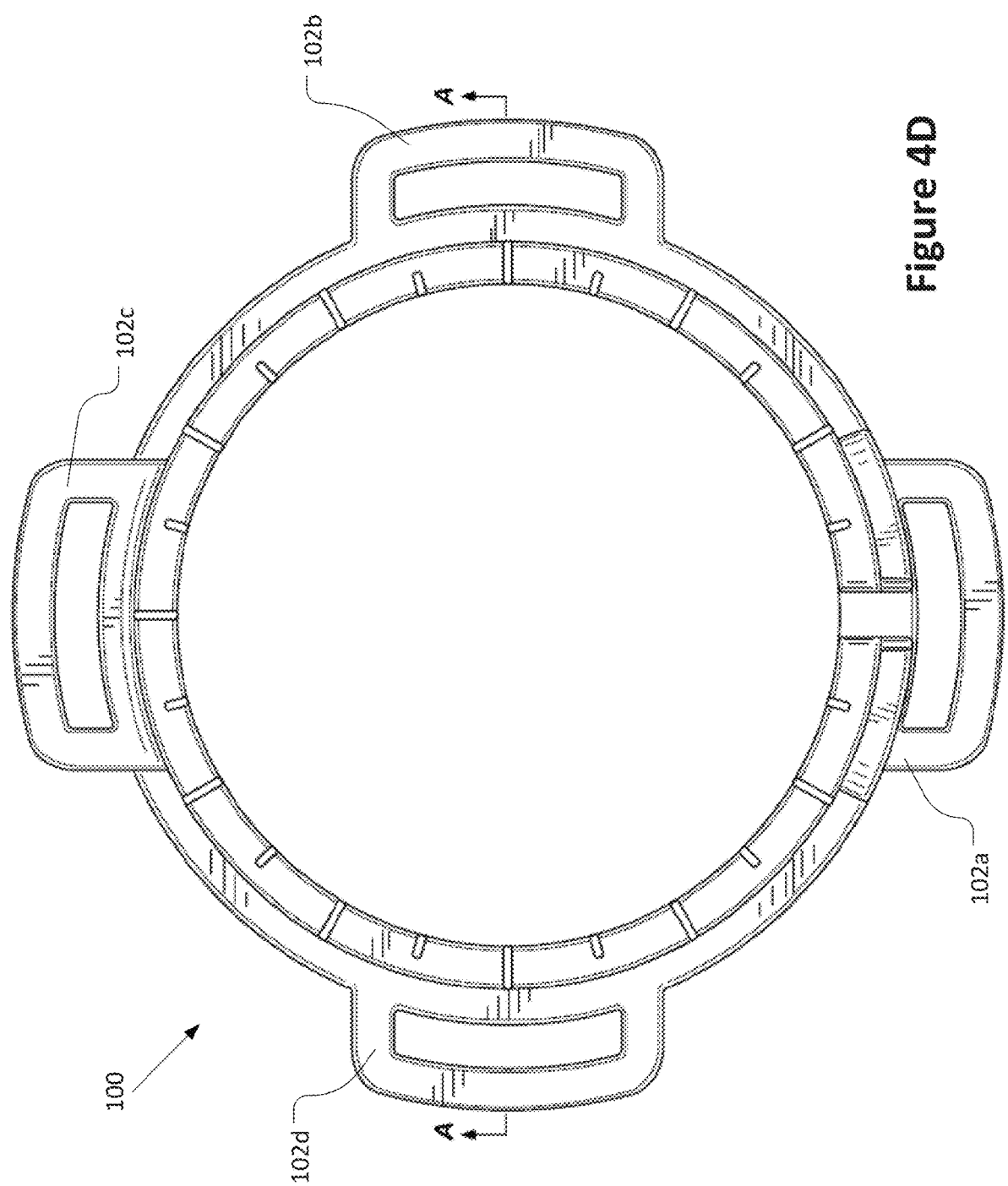

ULTRASONIC TRANSDUCER TREATMENT DEVICE

TECHNICAL FIELD

Embodiments herein relate to the field of ultrasonics, and more particularly to ultrasonic transducer treatment devices and associated systems and methods.

BACKGROUND

Ultrasonic treatment is used to treat various conditions, such as neurological conditions. During treatment, a certain level of ultrasound energy needs to be delivered to a specific area in the brain. The ultrasound energy has to be delivered through the bone of the skull and focused on the desired region within the skull. Reliable positioning and aiming of the ultrasound transducer on the patient's skull is a key requirement of the treatment process. The treatments are typically carried out using a magnetic resonance imaging (MRI) system to image the brain and show the operator the region to be treated.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIG. 4D illustrates a top view of the transducer holder of FIG. 4A in accordance with various embodiments.

DETAILED DESCRIPTION OF DISCLOSED EMBODIMENTS

Figure 1A:
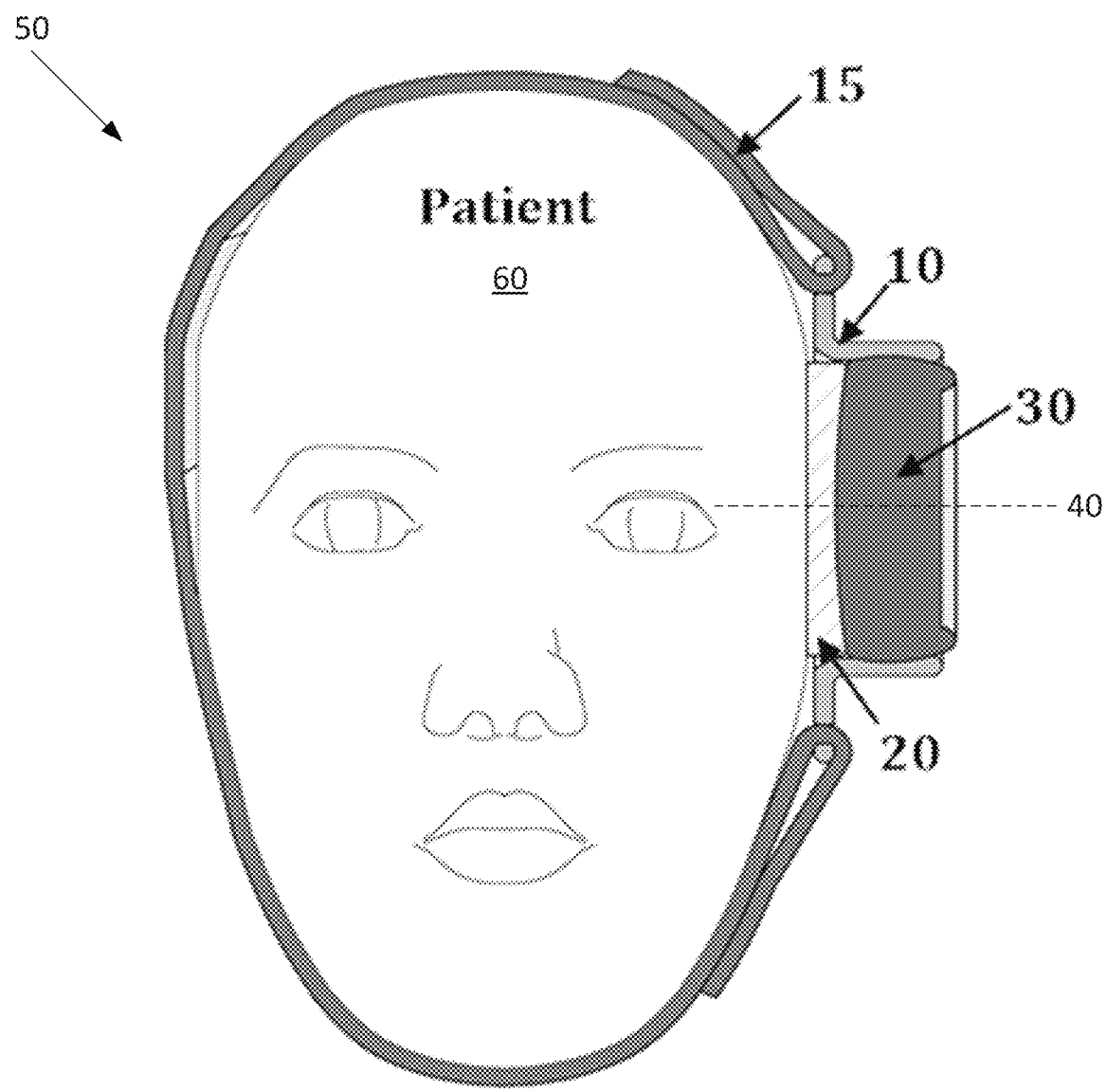
FIG. 1A schematically illustrates an ultrasonic treatment device with a transducer holder holding an ultrasonic transducer at a first angle (e.g., a 0-degree angle), in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other. Additionally, the term "acoustically coupled" may be used herein to describe that two or more elements are arranged in a way to enable a signal (e.g., an ultrasonic signal), such as a wave or another type of signal, to pass from one element to another.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Various embodiments herein provide an ultrasonic treatment system that includes a transducer holder to hold an ultrasonic transducer (also referred to as an ultrasonic probe and/or transmitter). The transducer holder includes multiple mounting positions for the ultrasonic transducer to enable the transducer to be held by the transducer holder at different angles. For example, in some embodiments, the transducer holder may include multiple mounting elements on an interior surface of the transducer holder. The mounting elements may be, for example, ridges or grooves on the interior surface, hook-and-loop fasteners, and/or another means of interlocking. The transducer may include and/or be provided with one or more locking elements that interact with the mounting elements of the transducer holder to hold the transducer within the transducer holder. For example, in some embodiments, a locking assembly may be attached to (e.g., mounted on) the transducer to provide the locking elements.

In some embodiments, the locking elements may include a retractable element that may be retracted (e.g., by an actuator) to place the transducer into the desired position and then extended to interact with the ridge or groove of the corresponding mounting element and thereby hold the transducer in the desired position. In some embodiments, the locking elements of the transducer may be spring-loaded, such that they may be retracted by applying pressure to the actuator (e.g., manually) and then extended by releasing the pressure from the actuator.

In various embodiments, the mounting elements of the transducer holder may be circular elements that extend in a circle around the interior surface of the transducer holder. In one example, the plurality of mounting elements may be parallel to one another. Additionally, the transducer may include a first locking element and a second locking element. Accordingly, the transducer may be held by the transducer holder at an angle of zero degrees (with respect to a center line through the transducer holder in a direction that is orthogonal to a plane of the mounting elements) by mechanically engaging the first and second locking elements of the transducer to the same mounting element of the transducer holder. Additionally, the transducer may be held by the transducer holder at an angle by mechanically engaging the first locking element of the transducer to a first mounting element of the transducer holder and the second locking element of the transducer to a second mounting element of the transducer holder.

The angle of the transducer with respect to the transducer holder may be based on a spacing between the first and second mounting elements. The transducer holder may include any suitable number of two or more mounting elements to provide a desired number of possible angles at which the transducer may be arranged. For example, the transducer holder may include three mounting elements to provide three different possible angles. Additionally, the spacing between the mounting elements may be designed to provide desired values for the different possible angles, such as 0 degrees, 2.5 degrees, and/or 5 degrees. It will be apparent that other numbers of mounting elements and/or values of the possible angles may be used in accordance with various embodiments.

Additionally, or alternatively, the mounting elements may enable the angle of the transducer to be aimed in different directions. Accordingly, the angle of the ultrasonic beam generated by the transducer may be aimed toward the desired region of the patient. For example, in some embodiments, the locking mechanism may be rotated with respect to the transducer to enable the angle of the transducer to be aimed in different directions.

In other embodiments, the individual mounting elements may be disposed at different angles with respect to one another (not parallel) to provide different angles for the transducer.

In various embodiments, the transducer holder and/or transducer may further include one or more portions that are formed of a material that is visible in MRI images to provide a fiducial marker that enables the spatial orientation of the transducer to be determined from the MRI images.

The treatment device described herein may enable the ultrasonic transducer to be easily positioned by an operator at the desired angle and/or orientation, e.g., without tools and/or with tools that are compatible with use in or near MRI systems.

These and other embodiments will be described in further detail below with reference to the figures.

FIG. 1A schematically illustrates an ultrasonic treatment device 50 ("device 50") in accordance with various embodiments. The device 50 may include a transducer holder 10 that engages with a transducer 30 to hold the transducer 30 at a desired angle with respect to a reference line 40 through the center of the transducer holder 10. For example, the transducer is shown in FIG. 1A to be held at an angle of 0 degrees.

In various embodiments, the device 50 may further include one or more straps 15 attached to the transducer holder 10 to secure the transducer holder 10 (and thus the transducer 30) to a patient 60. The device 50 may further include an acoustic pad 20 (e.g., a solid gel pad) positioned between the transducer 30 and the patient 60 to acoustically couple the ultrasonic energy from the transducer 30 to the patient 60. In some embodiments, additional acoustic material (e.g., liquid gel) may be applied between the patient 60 and the acoustic pad 20.

Figure 1B:
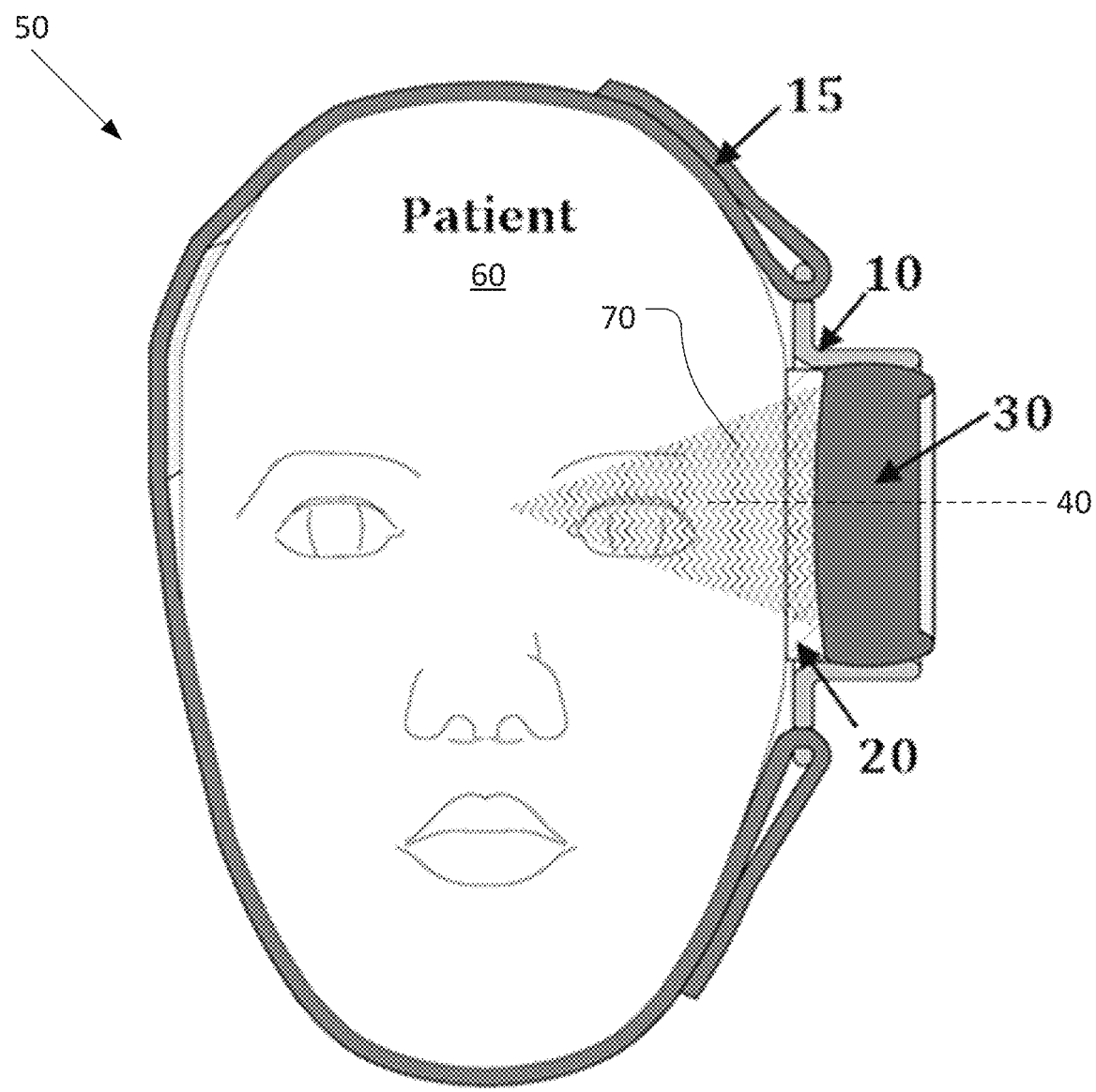
FIG. 1B illustrates the ultrasonic treatment device of FIG. 1A, showing a path of the ultrasonic beam from the transducer, in accordance with various embodiments.

FIG. 1B schematically illustrates the device 50 when the transducer 30 is generating an ultrasonic beam 70, in accordance with various embodiments. In some embodiments, the transducer 30 may be a circular, single element transducer to provide a spherically focused ultrasonic beam (e.g., with the general conical shape as shown in FIG. 1B). Those skilled in the art of ultrasound propagation will appreciate that the conical shape shown in FIG. 1B is a general representation, and that the actual ultrasound beam is more complicated than the simple conical shape of the illustration.

Figure 2A:
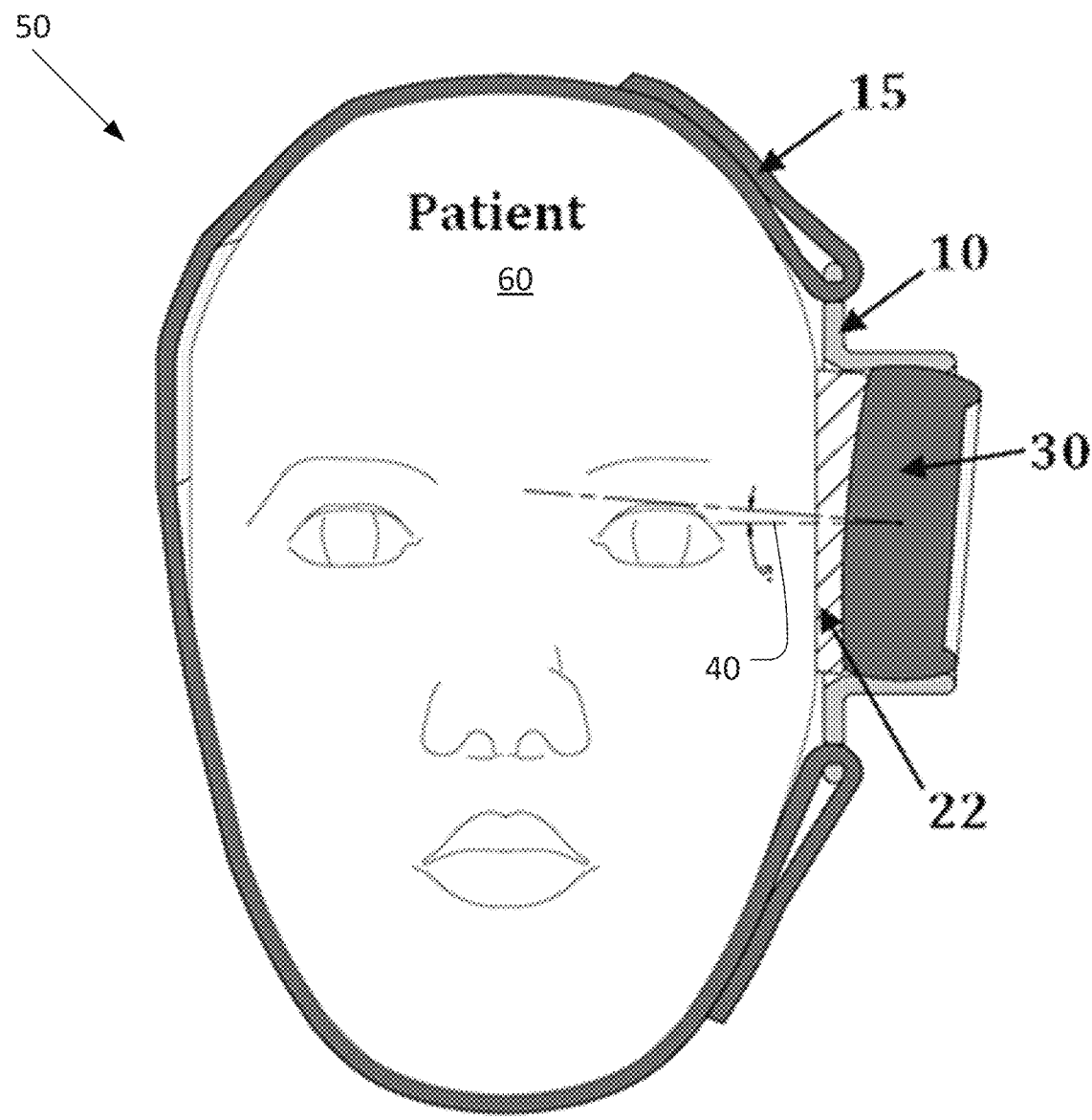
FIG. 2A illustrates an ultrasonic treatment device with a transducer holder holding an ultrasonic transducer at a second angle (e.g., a 5-degree angle), in accordance with various embodiments.

FIG. 2A illustrates the device 50 with the transducer 30 held by (e.g., within) the transducer holder 10 at an angle of 5 degrees relative to the reference line 40. An angled acoustic pad 22 may be used when the transducer 30 is oriented at an angle, in order to substantially fill the space between the transducer 30 and the patient 60, and provide for acoustic transmission from the transducer 30 to the patient 60.

Figure 2B:
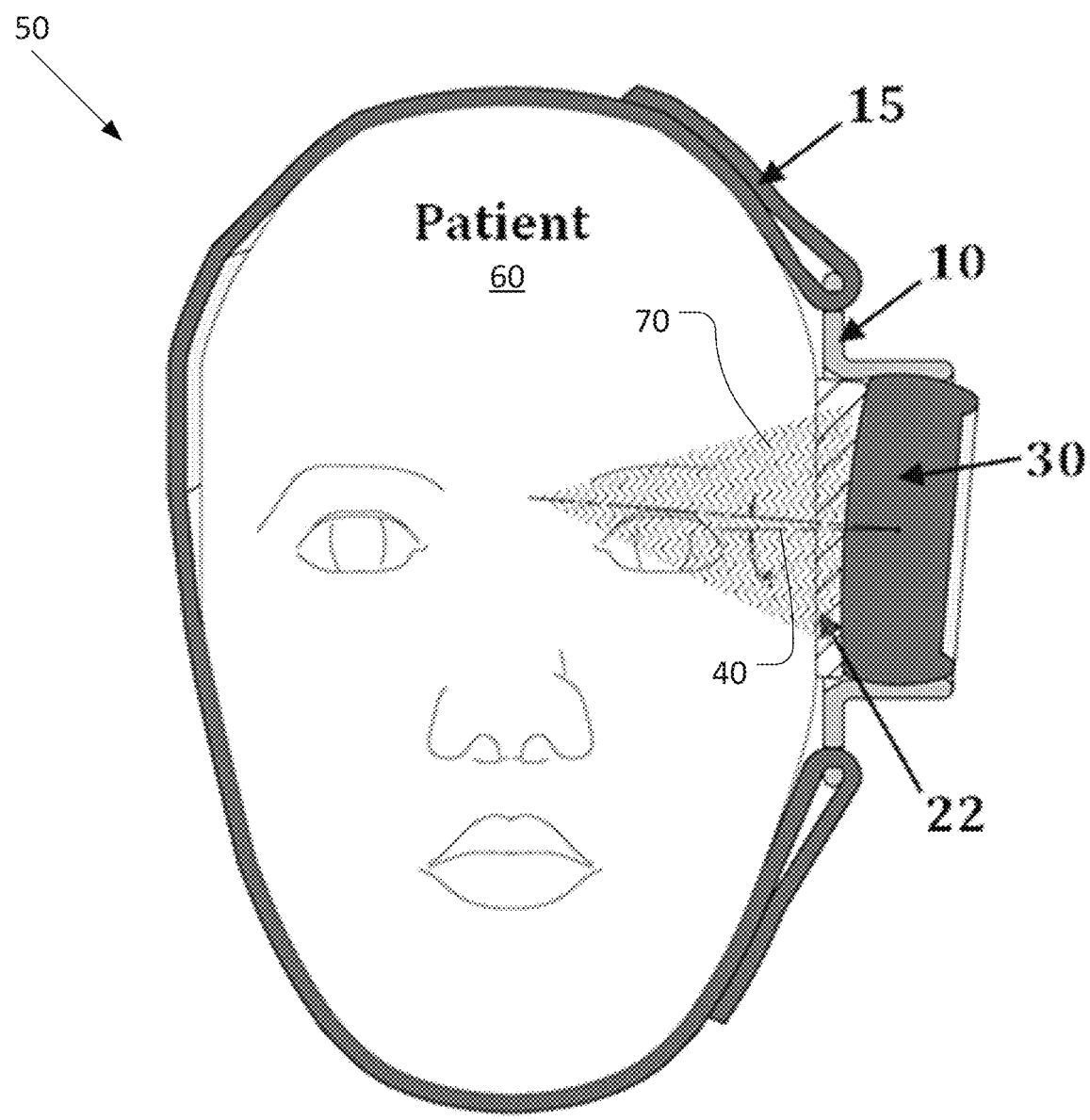
FIG. 2B illustrates the ultrasonic treatment device of FIG. 2A, showing a path of the ultrasonic beam from the transducer, in accordance with various embodiments.

FIG. 2B illustrates the ultrasonic beam 70 generated by the transducer 30 while held at the 5-degree angle. While the ultrasonic beam 70 is shown in FIG. 2B to be pointing upward into the patient 60, the angle of the transducer 30 may be directed to aim the beam 70 in a different direction.

Figure 3:
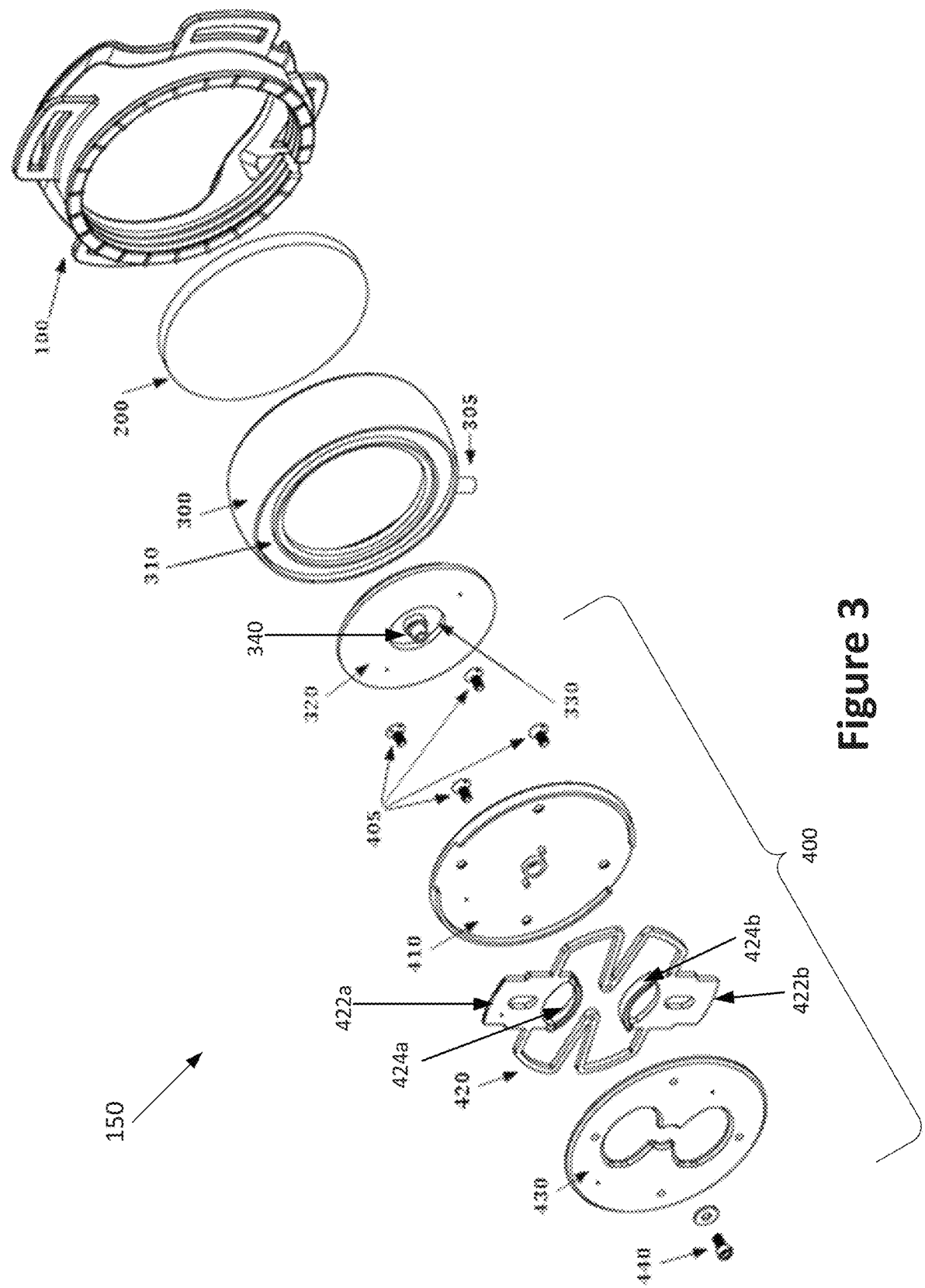
FIG. 3 is an exploded view of an ultrasonic treatment device, in accordance with various embodiments.
Figure 4A:
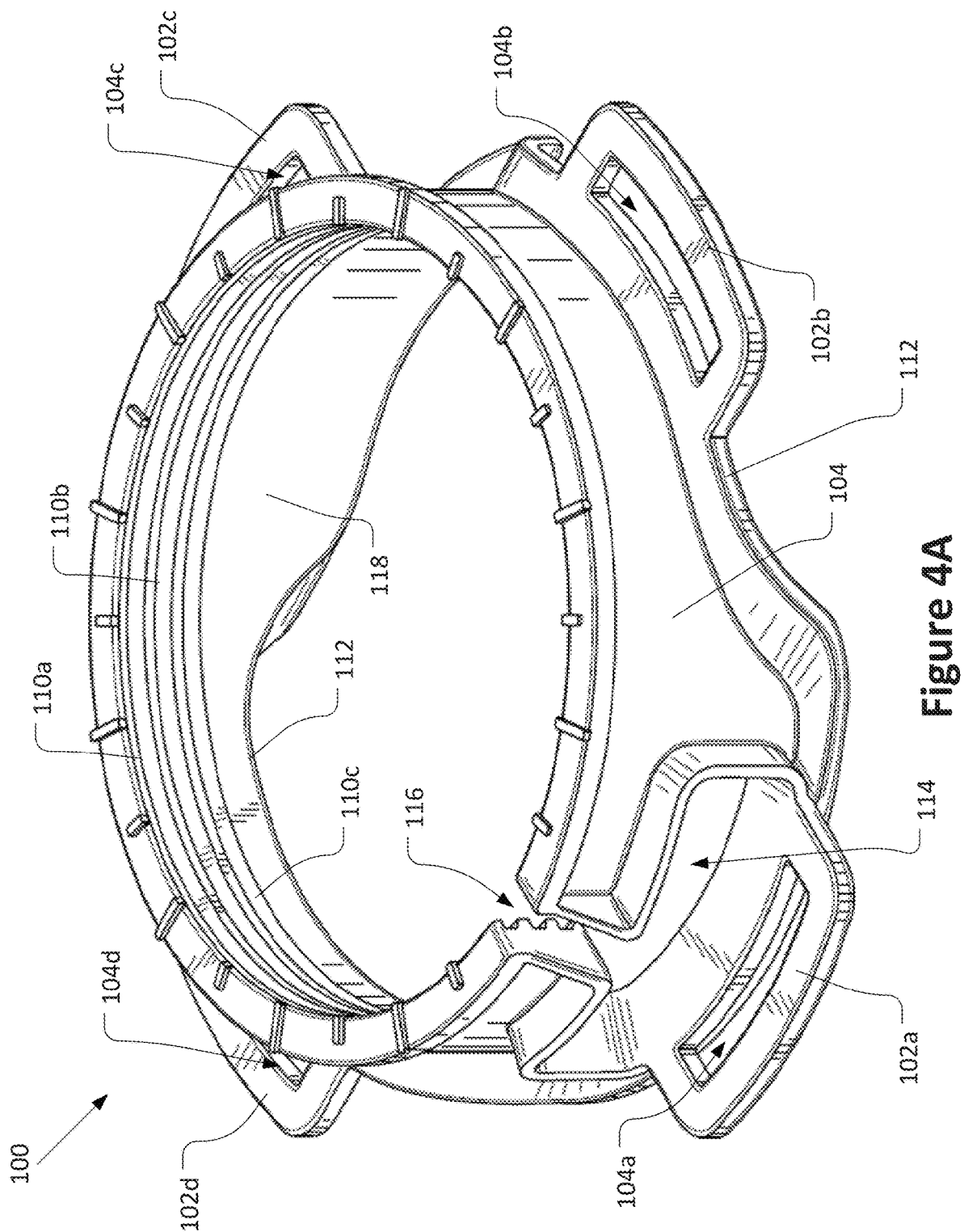
FIG. 4A illustrates a first perspective view of a transducer holder in accordance with various embodiments.
Figure 4B:
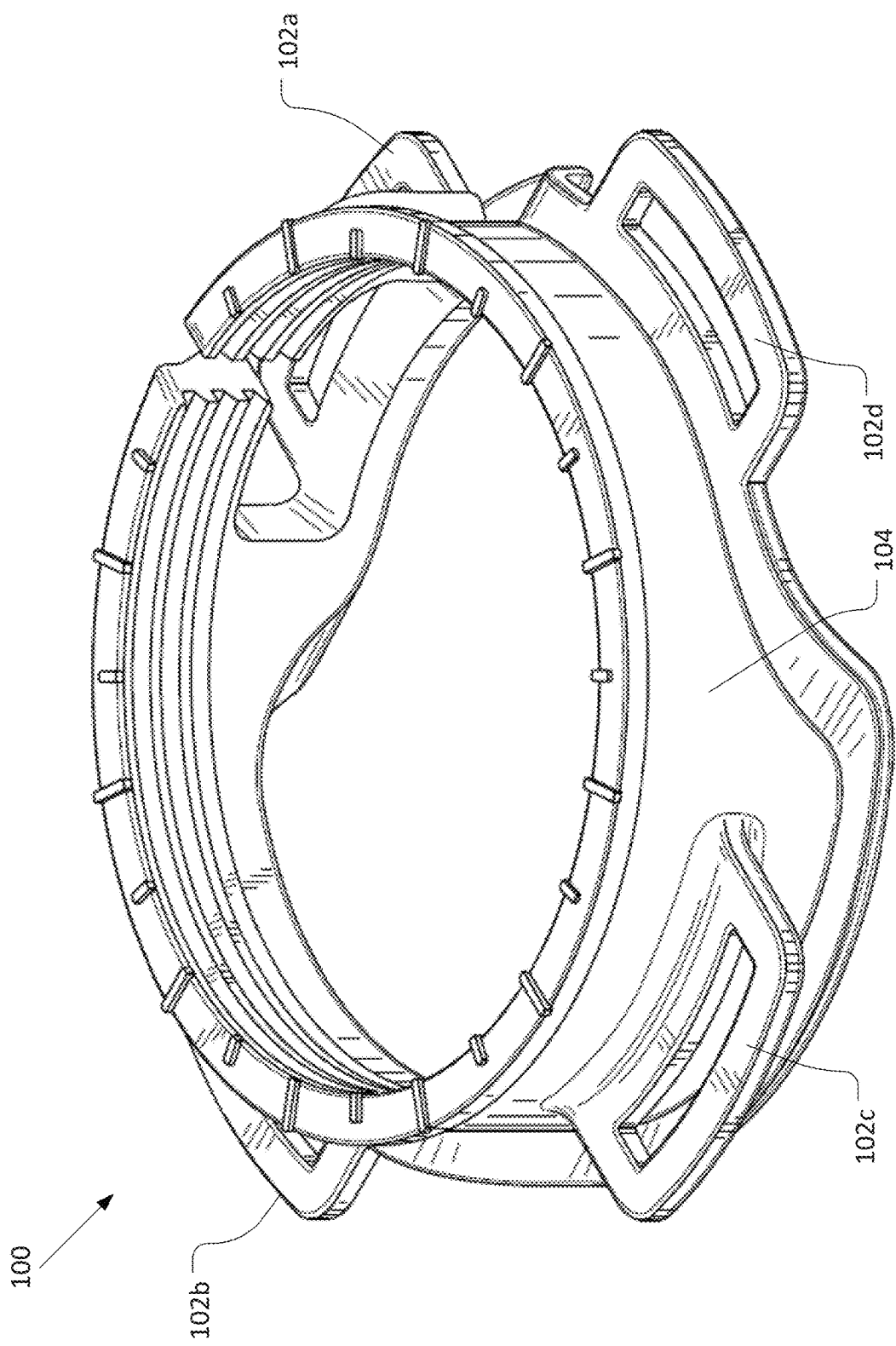
FIG. 4B illustrates a second perspective view of the transducer holder of FIG. 4A in accordance with various embodiments.
Figure 4C:
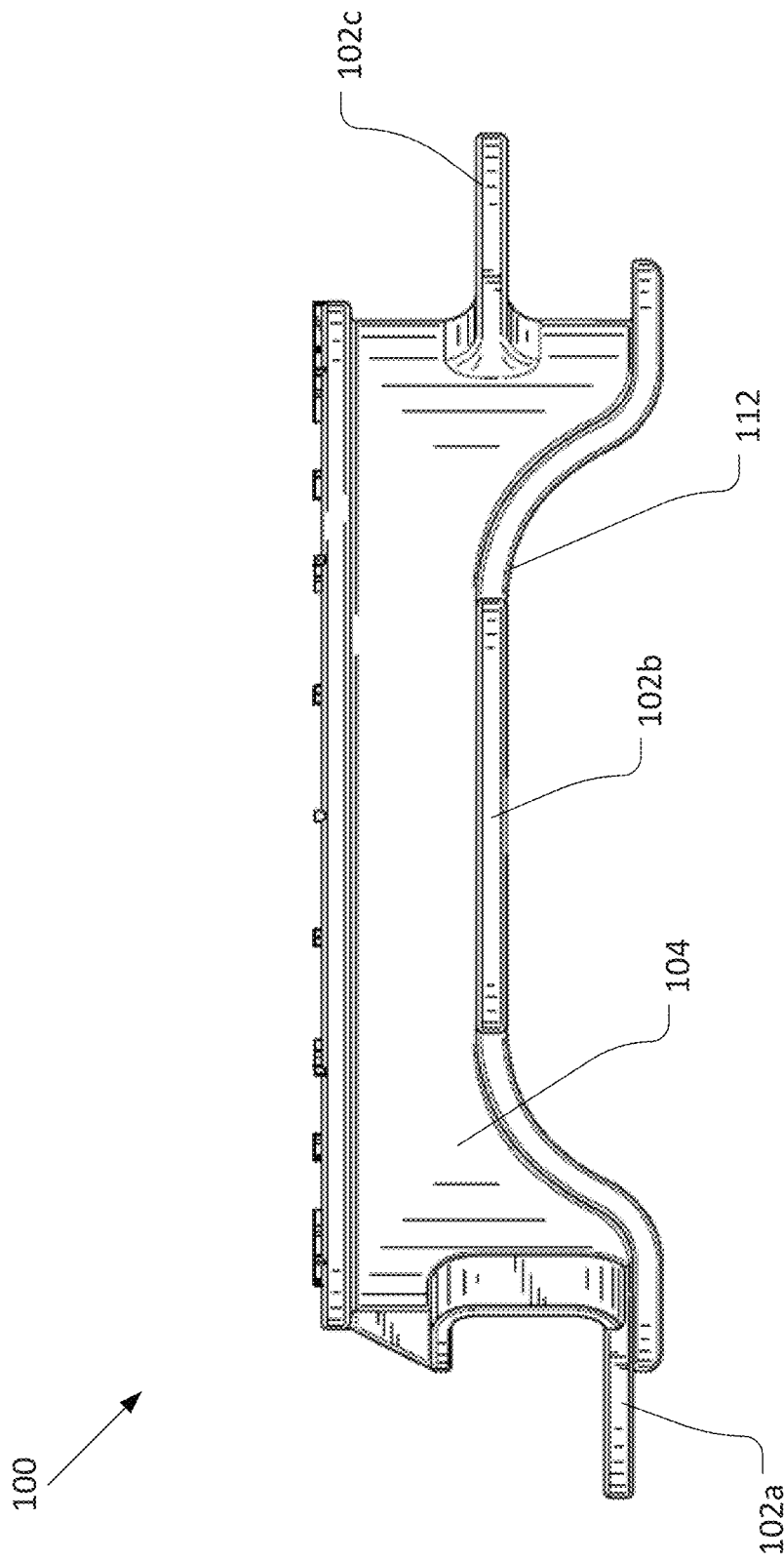
FIG. 4C illustrates a side view of the transducer holder of FIG. 4A in accordance with various embodiments.
Figure 4E:
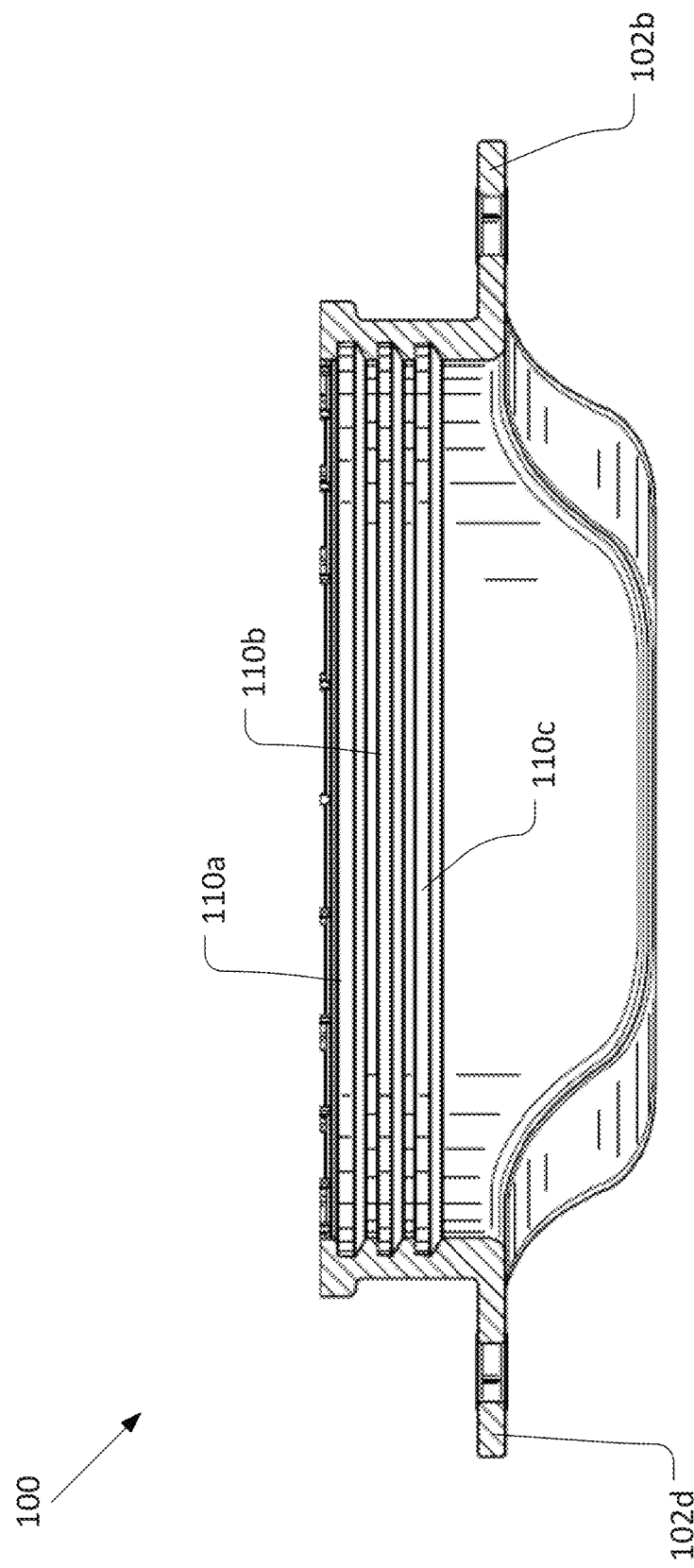
FIG. 4E illustrates a cross-sectional view of the transducer holder along the line A-A in FIG. 4D in accordance with various embodiments.

FIG. 3 is an exploded view of an ultrasonic treatment device 150 ("device 150") in accordance with various embodiments. The device 150 may depict one example implementation of the device 50 in more detail. The device 150 may include a transducer holder 100 (which may correspond to the transducer holder 10) and an ultrasonic transducer 300 (which may correspond to the transducer 30). The device 150 may further include a locking assembly 400 to couple the transducer 300 to the transducer holder 100 in a desired orientation. Additionally, the device 150 may include an acoustic pad 200 (e.g., gel pad) coupled to the transducer 300, e.g., to the bottom of the transducer 300 to be positioned between the transducer 300 and the patient 60).

Figure 5:
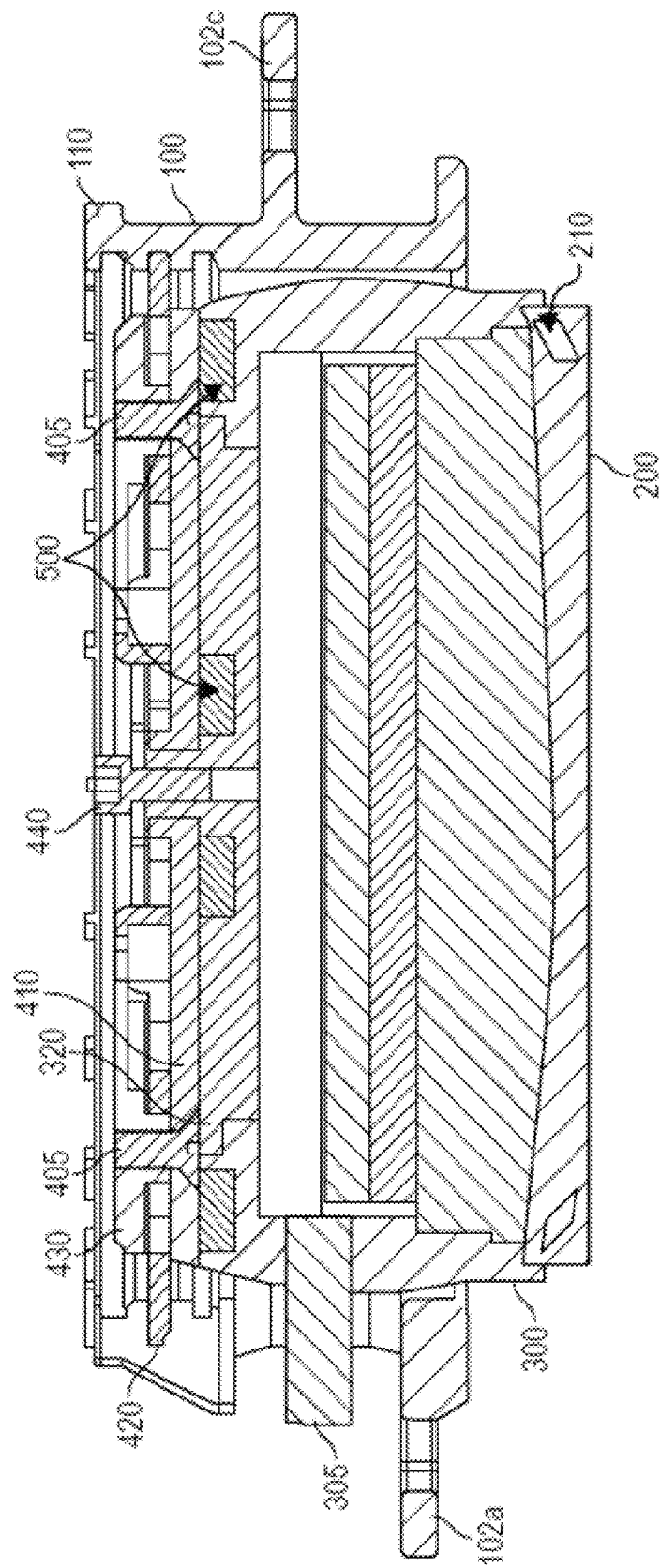
FIG. 5 illustrates a cross-sectional view of a transducer held by a transducer holder at a first angle (in this example, a 0-degree angle), in accordance with various embodiments.
Figure 6:
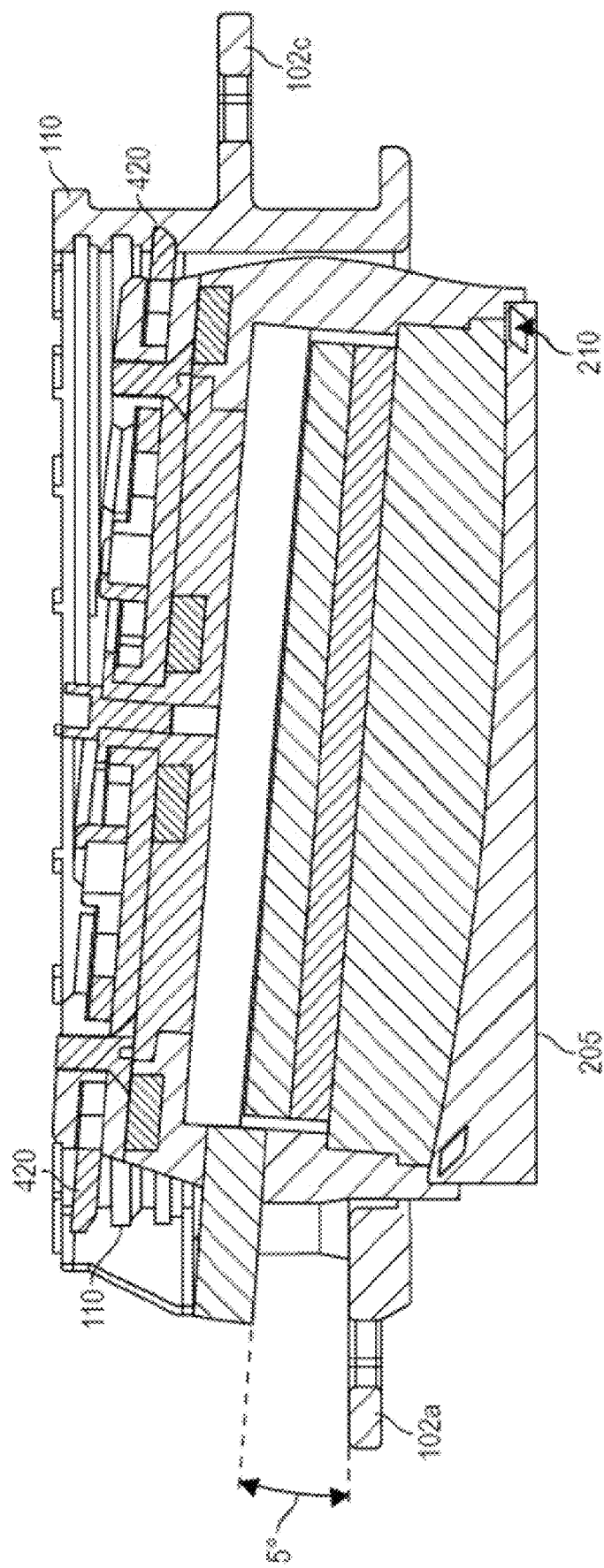
FIG. 6 illustrates a cross-sectional view of a transducer held by a transducer holder at a second angle (in this example, a 5-degree angle), in accordance with various embodiments.
Figure 7:
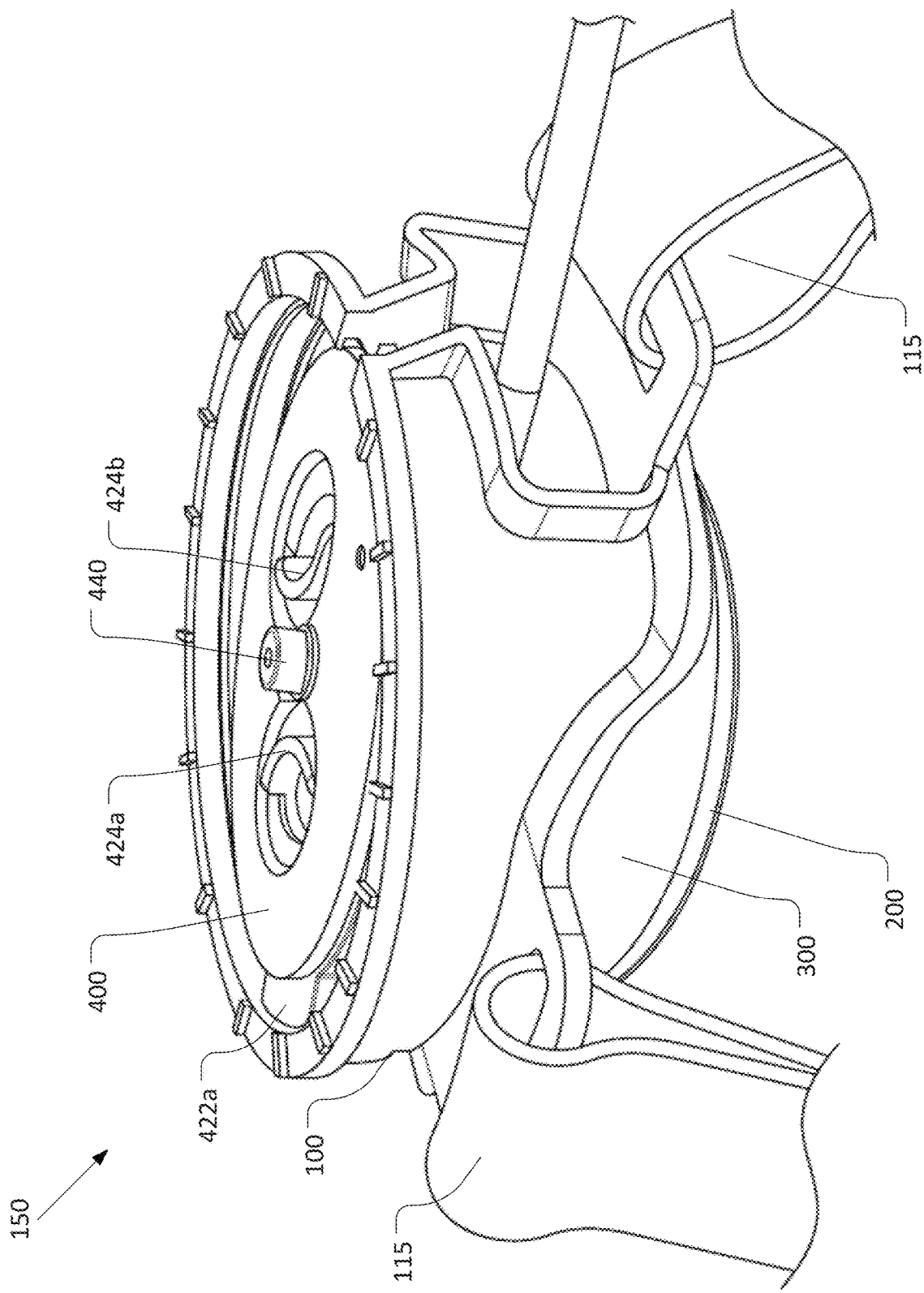
FIG. 7 is a top perspective view of an ultrasonic treatment device with the transducer held by the transducer holder at a second angle (in this example, a 5-degree angle), in accordance with various embodiments.

FIGS. 4A-4E illustrate additional views of the transducer holder 100. FIG. 5 illustrates a cross-sectional view of the transducer 300 held by (e.g., within) the transducer holder at a 0-degree angle, as further discussed below. Additionally, FIG. 6 illustrates a cross-sectional view of the transducer 300 held by (e.g., within) the transducer holder 100 at a 5-degree angle. Furthermore, FIG. 7 is a perspective view of the device 150 with the transducer 300 held by the transducer holder 100 at a 5-degree angle.

As shown in FIGS. 4A-4E, the transducer holder 100 may include flanges 102a-d that extend out from a body 104 of the transducer holder 100 and include openings 106a-d. The flanges 102a-d may enable the transducer holder 100 to be coupled to the patient, e.g., using one or more straps (not shown in FIGS. 4A-4E). For example, the one or more straps may be similar to strap 15 shown in FIGS. 1A-B and 2A-B, and/or straps 115 shown in FIG. 7. The four flanges 102a-d may enable the transducer holder 100 to be coupled to the patient with straps that go around the patient in two directions. For example, one strap may go across the patient's forehead and around the back of the patient's head, and another strap may go around the top of the patient's head and under the patient's chin.

In some embodiments, one or more of the flanges 102a-d may be positioned above a bottom plane of the transducer holder 100 that is to be in contact with the patient when the transducer holder 100 is secured to the patient. For example, as shown in FIGS. 4A-4E, flanges 102b-d may be positioned at a greater height (e.g., the same height) from the bottom plane than the flange 102a (which is below opening 114, further discussed below). Additionally, in some embodiments, one or more portions 112 of the bottom surface 108 may extend up from a contact plane with the patient. These features of the transducer holder 100 may enable the transducer holder 100 to comfortably fit over the patient's ear in some embodiments and/or use cases.

Additionally, or alternatively, the flanges 102a-d may be oriented symmetrically around the transducer holder 100, e.g., with respect to a vertical plane through the center of the transducer holder 100. For example, flanges 102b and 102d may be symmetrically located, as shown in FIGS. 4A-B and 4D-E. This may enable the transducer holder 100 to be used on either side of the patient's head.

It will be apparent that other embodiments may include a different number of flanges 102-d and/or different positions of the flanges (e.g., height from the contact plane and/or angular location around the transducer holder 100). For example, the number and/or position of the flanges 102a-d may be modified for use of the transducer holder on a different location on the patient's body.

The transducer holder 100 may further include an opening 114 with a slot 116 to enable the cable of the transducer 300 (discussed further below) to pass through the slot 116 when the transducer 300 is placed in the transducer holder 100 and exit through the opening 114 while in position.

In various embodiments, the transducer holder 100 may include a plurality of mating elements 110a-c on an inner surface 118 of the transducer holder 100. The mating elements 110a-c may engage with locking elements of the transducer 300 to hold the transducer 300 within the transducer holder 100, as discussed further below.

In some embodiments, the mating elements 110a-c may include grooves, as shown in FIGS. 3-6. In some embodiments, the grooves may be parallel to one another. The grooves may extend around all or most of the inner surface 118 of the transducer holder, e.g., interrupted by the slot 116. For example, the grooves may extend around at least 75% of the circumference of the inner surface 118, such as at least 90% of the circumference. The individual grooves may be formed by a pair of ridges that form the respective groove between them. For example, four ridges may form three grooves. It will be apparent that other designs and/or physical attributes of the mating elements 110a-c and corresponding locking elements 4222a-b may be used.

The transducer holder 100 may include any suitable materials, such as urethane methacrylate. This material may provide a desirable combination of stiffness, low weight, MRI safety, and invisibility in MRI images. However, it will be apparent that other materials may be included in the transducer holder 100 in addition to or instead of urethane methacrylate. In some embodiments, the transducer holder 100 may be generated by three-dimensional (3D) printing.

In various embodiments, the transducer 300 may generate ultrasound energy to be delivered to the patient. For example, the transducer 300 may be controlled by electrical drive signals received via a control interface 305 (e.g., a cable). In some embodiments, the cable may be at least 3 meters in length to connect to an electronic drive device that operates the transducer 300. In some embodiments, the transducer 300 may be a circular single element transducer to provide a spherically-focused ultrasonic beam. For example, the transducer 300 may be in the shape of a hollow cylinder.

Different transducers 300 may be used with the other elements of the device 150. For example, in some embodiments, the device 150 may employ different transducers 300 having the same aperture (e.g., 60 mm or another suitable aperture) and different focal lengths (e.g., a nominal radius of curvature (ROC) of 55 mm, 65 mm, 80 mm, and/or another suitable value). The different focal lengths may be used to target different regions of the brain.

In some embodiments, the transducer 300 may use a 1-3 piezoelectric material with a low loss backing to provide a desired bandwidth (e.g., about 21% or another suitable value for low power, non-imaging purposes). The measured focal peak pressure locations are typically found 1-2 mm shallower than the nominal transducer ROC.

It will be apparent that other types and/or configurations of the transducer 300 may be used, depending on the application and/or treatment. For example, the transducer 300 may have any suitable diameter, frequency, and/or focal length.

The transducer 300 may include a cover plate 320 over the top opening of the transducer 300. The transducer 300 may include one or more portions that are formed of a material that is visible (e.g., bright) on MRI images to provide a fiducial marker that enables determination of the spatial orientation of the transducer 300. For example, in some embodiments, a ring 310 on the transducer 300 (e.g., an interior top edge of the opening in the transducer 300) and/or a ring 330 on the cover plate 320 may include the MRI-visible material. The MRI-visible material may be any suitable material that is visible on MRI images and compatible with MRI imaging, such as Styrene block polymer.

The cover plate 320 may further include a receptacle 340 to receive a screw 440 that couples the locking assembly 400 to the transducer 300. The locking assembly 400 may include a locking plate 420 that includes locking elements 422a-b. The locking elements 422a-b may be retractable from an extended position to a retracted position by pulling respective actuators 424a-b toward the center of the locking plate 420. The locking elements 422a-b may be spring-loaded, so that they move from the retracted position to the extended position when the pressure on the respective actuators 424a-b is released.

In some embodiments, the locking plate 420 may be positioned between housing plates 410 and 430 (e.g., using screws 405). The locking assembly 400 may be attached to the transducer 300 by the screw 440.

In some embodiments, the screw 440 may include an MRI-visible material, such as Styrene block polymer. Accordingly, the screw 440 may provide a fiducial marker to determine the position/orientation of the transducer 300 (e.g., in addition to or instead of the rings 310 and 330). In some embodiments, the screw 440 may include a cavity (e.g., in the center of the screw) that is filled with the MRI-visible material.

In various embodiments, the locking elements 422a-b may interact with the mounting elements 110a-c of the transducer holder 100 to hold the transducer 300 to the transducer holder 100 at a desired angle. For example, the locking elements 422a-b may be retracted and then extend into a groove of one of the mounting elements 110a-c. In some embodiments, the locking elements 422a-b may be coupled with the same mounting element 110a, 110b, or 110c to hold the transducer 300 at a first angle (e.g., 0 degrees) with respect to the transducer holder 100. Alternatively, the locking element 422a and 422b may be coupled to different mounting elements 110a-c to hold the transducer 300 at a different (e.g., non-zero) angle with respect to the transducer holder 100. For example, the locking element 422a may be engaged with the mounting element 110a and the locking element 422b may be engaged with the mounting element 110b to position the transducer at a second angle with respect to the transducer holder 100. Additionally, the locking element 422a may be engaged with the mounting element 110a and the locking element 422b may be engaged with the mounting element 110c to hold the transducer 300 at a third angle with respect to the transducer holder 100. The third angle may be greater than the second angle. For example, in one embodiment, the first angle may be 0 degrees, the second angle may be 2.5 degrees, and/or the third angle may be 5 degrees.

The value of the second and third angles may be based on the spacing between the mounting elements 110a-c. Additionally, the number of possible angles may be based on the number of mounting elements 110a-c. It will be apparent that other embodiments may use a different spacing between mounting elements 110a-c to provide different values of the mounting angles and/or a different number of mounting elements 110a-c to provide a different number of possible mounting angles.

In various embodiments, a non-zero angle of the transducer 300 may shift the location of the focal zone of the ultrasonic beam compared to a 0-degree angle. For example, for a nominal focal distance of 80 mm, the shifts are 3.5 mm for a 2.5-degree angle and 7 mm for a 5-degree angle. Since the focal zone may be about 4.4 mm wide in this example, the 7 mm shift translates into a shift of 1.6 times the beam diameter, or 3.2× the beam radius. The 2.5 degree angle accomplishes a nearly complete shift of the focal region to an adjacent location, and the 5 degree offset moves the focus completely to another location. The shift scales with the focal distance, so the value of the shift will be different for other focal distances.

One skilled in the art would comprehend that the spacing of the mounting elements (e.g., grooves) 110a-c may be arranged to provide corresponding shifts of the focal zone as may be desired, e.g., depending upon the focal distance and diameter of the focal region of the transducer 300. Shifts of less than one-half the beam diameter (equivalently, shift of less than a beam radius) may not be as useful, as there may not be enough of a shift to materially change the region of stimulation within the brain. Similarly, too large an angle may create shear waves within the skull, which negatively affects beam transmission.

In various embodiments, the transducer 300 and/or locking assembly 400 may be rotated to point the ultrasonic beam in the desired direction (e.g., when the transducer 300 is oriented at a non-zero angle). This rotation may be facilitated by the mounting elements 110a-c being parallel to one another. However, other embodiments may include two or more mounting elements 110a-c that are disposed at different angles (not parallel).

In some embodiments, the locking assembly 400 (e.g., locking plate 420) may rotate with respect to the transducer 300 to enable the transducer 300 to be mounted at different directions of angulation. This may enable the transducer 300 itself to maintain a position with the control interface 305 and/or associated cable to be aligned with the opening 114 of the transducer holder 100.

As discussed above, the acoustic pad 200 may be disposed between the transducer 300 and the patient to facilitate passage of the ultrasonic energy from the transducer 300 to the patient. The acoustic pad 200 may fit within the bottom of the transducer holder 100. In some embodiments, the acoustic pad 200 may be preformed at an angle (e.g., the first, second, or third angle described above) to provide acoustic coupling when the transducer 300 is oriented at that angle. Accordingly, different acoustic pads 200 may be used for different angles of the transducer 300. In some embodiments, the acoustic pads 200 may be color-coded according to the angle that they provide.

The acoustic pad 200 may include and/or be provided with an acoustic gel. For example, in some embodiments, acoustic gel may be applied to one or both sides of the acoustic pad 200. In some embodiments, the acoustic pad 200 may include styrene block polymer and/or another material that is visible in MRI images. The MRI visibility of the acoustic pad 200 may provide another source of reference to determine the positioning of the transducer 300.

In some embodiments, the acoustic pad 200 may include a rim 210 mechanically associated with (e.g., embedded into) a top surface of the acoustic pad 200 to maintain the acoustic pad 200 in place adjacent to the transducer 300. For example, the rim 210 may couple to a corresponding rim on the bottom edge of the transducer 300. The rim 210 may be designed so as not to interfere with the propagation of the ultrasound signal from transducer 300 into patient 60, either by choice of material composition of rim 210, or selection of the inner diameter of rim 210 so as not to be in the path of the ultrasound beam 70.

Figure 8:
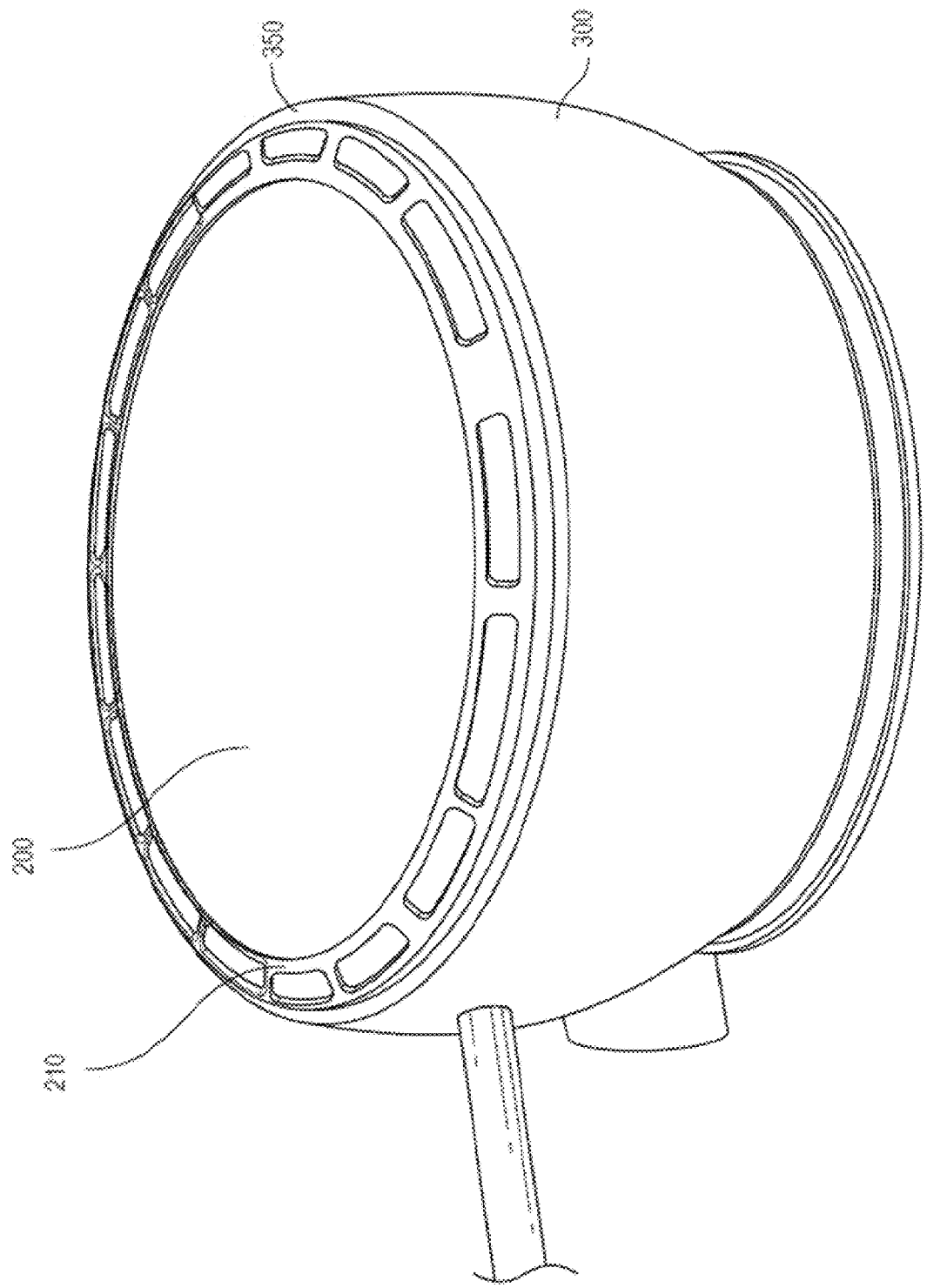
FIG. 8 illustrates a bottom perspective view of an acoustic pad attached and acoustically coupled to a transducer, in accordance with various embodiments.

FIG. 8 is a bottom perspective view of the acoustic pad 200 positioned on the bottom of the transducer 300, showing the rim 210 engaged with the bottom rim 350 of the transducer. The rim 210 may prevent the acoustic pad 200 from slipping off the bottom surface of the transducer, which may be especially prone to happen with angled positions of the transducer 300.

Figure 9:
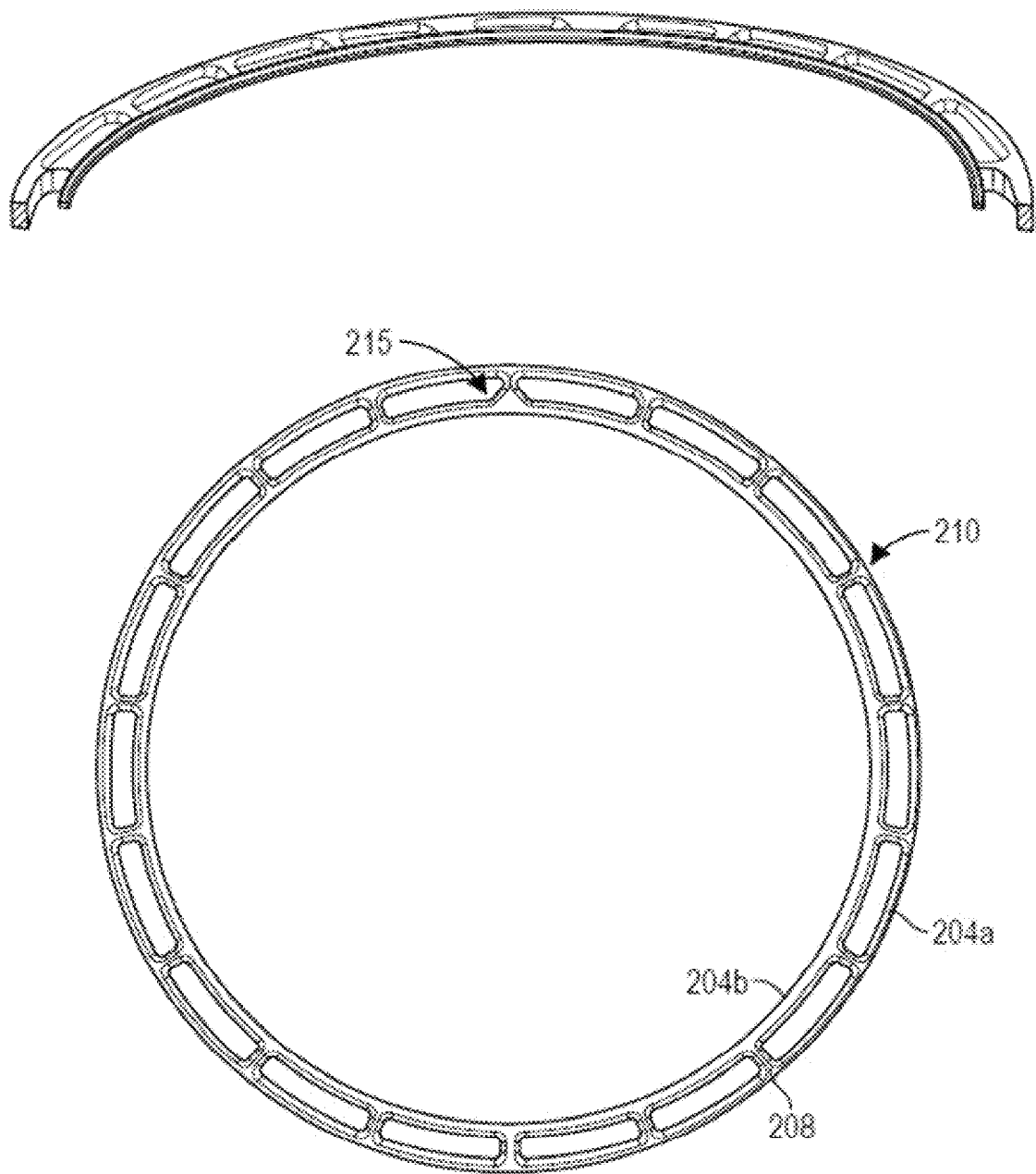
FIG. 9 illustrates a top view and a partial perspective view of a rim that may be mechanically associated with (e.g., embedded in) an acoustic pad to facilitate maintenance of the acoustic pad's position adjacent the transducer.

FIG. 9 illustrates the rim 210 in more detail, in accordance with some embodiments. For example, the rim may include two circular portions 204 that are connected by multiple connecting portions 208. In some embodiments, the rim 210 may further include an alignment feature 215 to enable determination of the direction of the angled slope of the acoustic pad 200. For example, the alignment feature 215 may be aligned with the thickest portion of the acoustic pad 200. The alignment feature 215 may not be needed for a 0-degree acoustic pad 200. The alignment feature 215 may be a physical feature that is visually distinguishable, such as a connecting portion that is different from the other connecting portions 208 of the rim 210.

The rim 210 may be made of any suitable material. For example, in some embodiments, the rim 210 may be made of plastic, e.g., 3-D printed, such as Fused Deposition Modeling (FDM) Ultem 9085.

In some embodiments, the fiducial marking features additionally or alternatively include optical sensing features coupled to the transducer 300 (e.g., the back of the transducer 300, such as the cover plate 320). The optical sensing features may include individual targets, such as multiple small spherical targets arranged in a triangular or other pattern in space behind transducer 300. The targets may be imaged by one or more optical detection devices such as one or more cameras. By comparing the position of these optical targets with the known central axis of the transducer 300, it is possible to align the transducer 300 in space relative to the patient's head or other body part without the use of an MRI system. Such an optical system may need information on the spatial location of the patient's head, which may be done with the previously mentioned optical targets, as well as some internal mapping of the patient's brain or other body part from a separately obtained scan, such as a MRI or medical CT scan.

One skilled in the art will recognize that there are other methods of such external optical marking, such as bar codes, QR codes, light emitting diodes (LEDs), or other patterns to be placed on the transducer 300, the holder 100, and/or the patient.

One skilled in the art will also recognize that another method of positioning the transducer may be used, such as external LEDs viewed by multiple cameras or external sound sources detected by multiple microphones.

A further extension of the fiducial marking system may use external physical measurements of the patient's head or other body region to determine the required position and angle of the transducer.

In accordance with various embodiments herein, the device 150 described herein may enable the angle of the transducer 300 to be easily adjusted to be one of a predefined set of angles with respect to the transducer holder 100. Additionally, the circumferential nature of the mounting elements 110a-c enables the angled beam of the transducer to be pointed in a desired direction. For example, the locking assembly 400 may be rotated to point the angled transducer 300 in a desired direction.

Furthermore, the compact design of the device 150 may enable the device 150 to be used within an MRI head coil. Additionally, the device 150 may include integrated fiducial markers, such as the rings 310 and/or 330, the screw 440, and/or the acoustic pad 200.

Experimental Results

Figure 10:
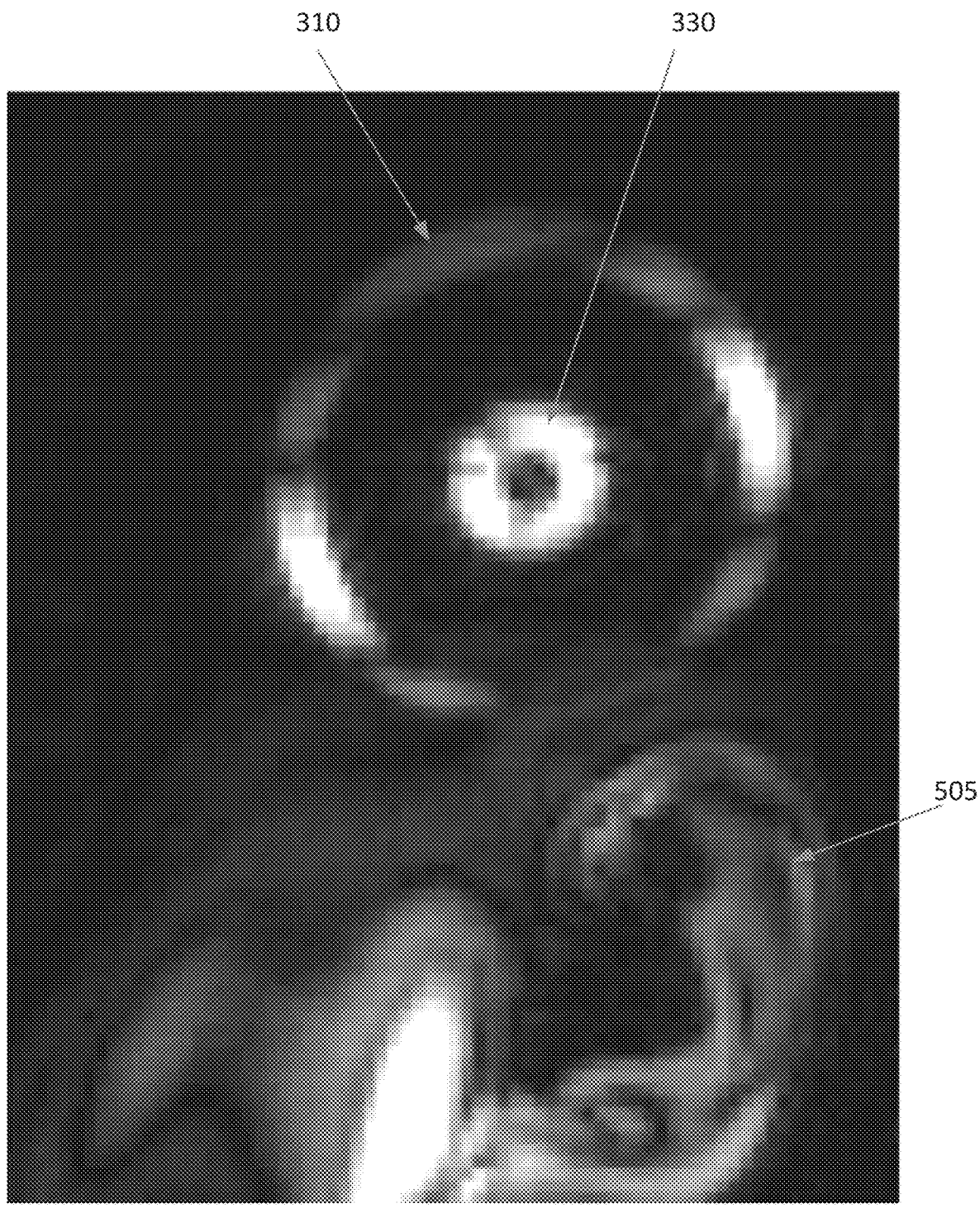
FIG. 10 is a magnetic resonance imaging (MRI) image that illustrates the transducer in relationship to a subject's ear, in accordance with various embodiments.

FIGS. 10-13 illustrate experimental results obtained using the devices and methods described herein (e.g., the device 50 and/or device 150), in accordance with various embodiments. FIGS. 10-13 are MRI images of test subjects undergoing treatment using low-intensity focused ultrasound pulsation (LIFUP) with the transducer 300 and transducer holder 100 herein disclosed. The MRI images were not acquired perfectly perpendicular to the fiducial rings, but were rotated after acquisition to facilitate targeting. FIG. 10 shows the transducer 300 in relationship to the subject's ear 500. The two fiducial rings 310 and 330 are clearly visible in the image.

Figure 11:
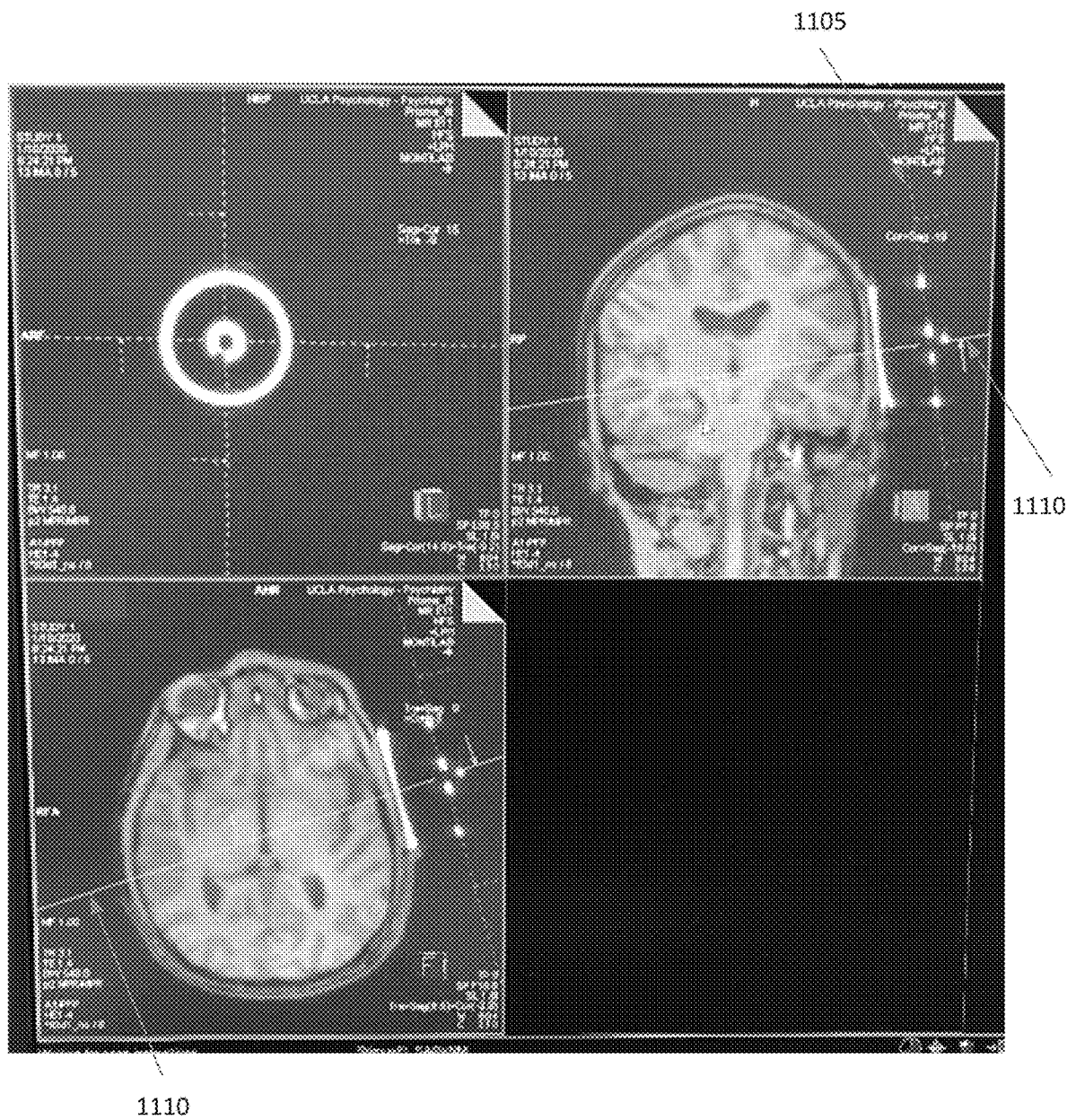
FIG. 11 illustrates MRI images to demonstrate an alignment process in accordance with various embodiments.

FIG. 11 illustrates the alignment process. The center of the concentric rings (fiducial markers 310 and 330) locates the axis of the ultrasound beam (upper left image). The line 1105 in the upper right and bottom images delineates the plane of the rings 310 and 330 and transducer 300. A line drawn perpendicular to the plane of the rings through the center screw 440 (e.g., line 1110 in the upper right and bottom images) established the central acoustic axis. The position of acoustic focus within the brain can be estimated using the measured transducer focal depth (which depends upon the design characteristics of the transducer 300 as required by the clinical circumstance) placed along the line of the acoustic axis determined using the fiducial markers. The gel pads used for acoustic coupling also are highly visible within the MRI image, making it easier to determine the exact position of the transducer and skull surfaces.

Figure 12:
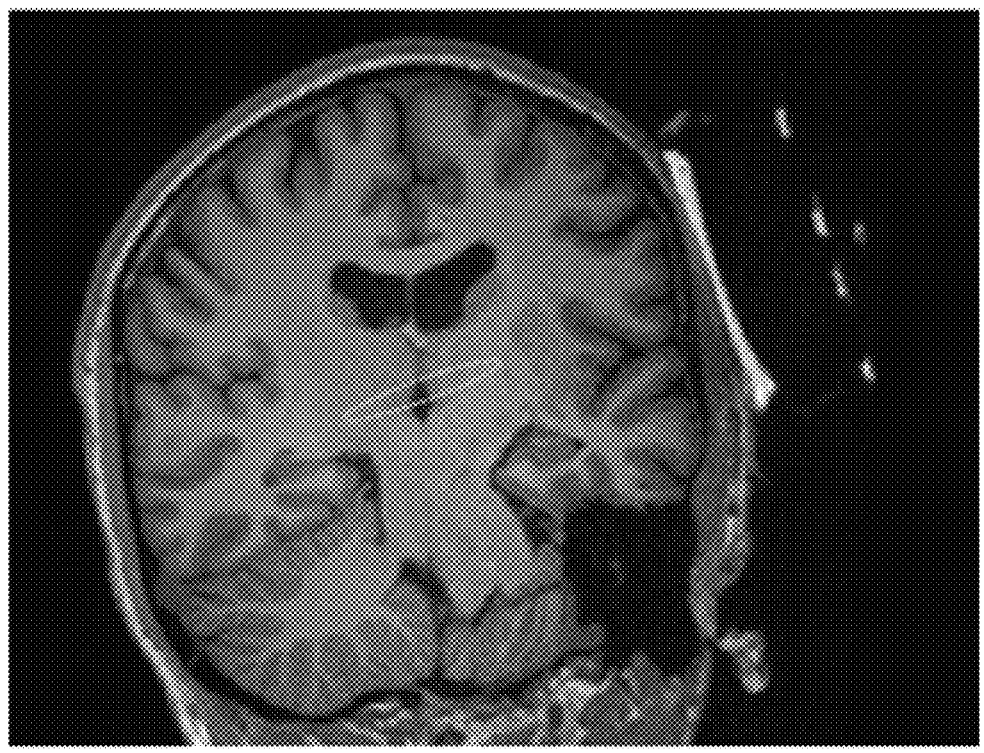
FIG. 12 illustrates an MRI image from FIG. 11 with an oval to indicate the focal location based on hydrophone measurements taken in water, in accordance with various embodiments.

FIG. 12 shows an overlay of the FIG. 11 image, with an oval that represents the focal location based on hydrophone measurements taken in water. The actual focal zone in-situ would be broader in width (due to distortion from bone) and shallower in depth (due to attenuation of the ultrasound along the direction of propagation). However, this gives the operator a general sense of the volume to be insonified. Based on images like FIG. 12, the operator may determine whether the transducer 300 is aimed at the desired location within the brain. The desired location depends upon the patient condition to be treated.

Figure 13B:
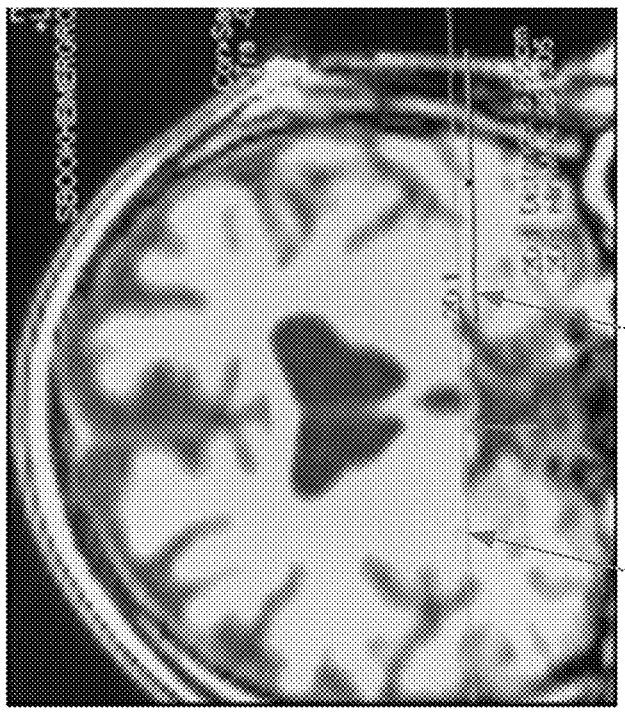
FIG. 13B is an MRI image that shows Low Intensity Focused Ultrasound Pulsation (LIFUP)-induced changes in cerebral blood flow in response to ultrasonic treatment, in accordance with various embodiments.
Figure 13A:
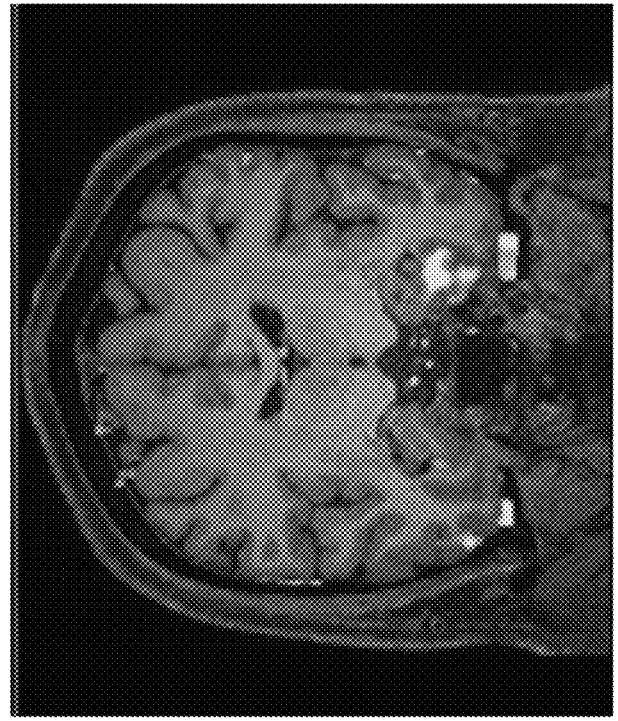
FIG. 13A is an MRI image to illustrate a targeting process, in accordance with various embodiments.

FIGS. 13A and 13B show an example of localized stimulation of brain tissue using Low Intensity Focused Ultrasound Pulsations (LIFUP). This is a representative sample image from a single subject recruited under an IRB-approved study (IRB: 18-000104). FIG. 13A shows the targeting process, with the center of the acoustic axis shown by line 1305 (compare to FIG. 11). A separate line 1310 is superimposed to show the approximate location of the focal region for the transducer used in this study (65 mm). This corresponds to the center of the oval region delineated in FIG. 12.

FIG. 13B shows LIFUP-induced changes in cerebral blood flow (CBF) as measured using pulsed arterial spin labeling (1.5×1.5×3 mm voxels, TR=4600 ms, TE=16.18 ms, TI=1990 ms, BD=700 ms, FAIR QII perfusion, 3D turbo GRASE sequence, turbo factor=20) collected using a Siemens 3T Prisma scanner. The ASL images are acquired before and after LIFUP stimulation. The resultant sequences are processed using FSL v 6.0.1 (FMRIB Software Library, Oxford, UK), and then subtracted to create a subtraction image. This is then is overlaid on a high resolution structural T1-weighted image, in order to generate the image seen in FIG. 13B.

The transducer used in this study has a 65 mm focal depth, with 61 mm diameter. The ultrasound transmit parameters were 942 mW/cm$^2$ I$_{spta.0}$ (720 mW/cm$^2$ Ispta.$_3$), 100 Hz PRF, 5% Duty Cycle, 0.71 MPa p$_{r.0}$ and 30 s on/30 s off for one 10 minute treatment block. The resultant change in the entorhinal cortex is in the focal region. The activations near the focus are presumed to be a direct effect of the LIFUP, while the other activations are presumed to be indirect effects via the functional connectivity of the focal region. Note that some of the apparent activations in this particular slice are not in the brain itself.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. An ultrasonic treatment device comprising:
    a transducer holder including:
        a circular body having an inner surface that is cylindrical; and
        a plurality of mating elements that extend around the inner surface at different heights from a bottom of the transducer holder, wherein the plurality of mating elements includes three or more mating elements including at least a first mating element, a second mating element, and a third mating element, and wherein the mating elements include respective grooves or ridges that do not connect with one another; and
    a locking assembly to be attached to an ultrasonic transducer, wherein the locking assembly includes a first locking element and a second locking element that are each adapted to engage with any of the plurality of mating elements to hold the ultrasonic transducer at a selected angle, from a plurality of predefined, non-continuous angles enabled by the plurality of mating elements, with respect to the transducer holder, wherein the locking assembly is to:
    hold the ultrasonic transducer at a first predefined angle when the first and second locking elements are both engaged with the first mating element;
    hold the ultrasonic transducer at a second predefined angle when the first locking element is engaged with the first mating element and the second locking element is engaged with the second mating element; and
    hold the ultrasonic transducer at a third predefined angle when the first locking element is engaged with the first mating element and the second locking element is engaged with the third mating element.

2. The ultrasonic treatment device of claim 1, wherein the first predefined angle is 0 degrees.

3. The ultrasonic treatment device of claim 2, wherein the second predefined angle is 2.5 degrees and the third predefined angle is 5 degrees.

4. The ultrasonic treatment device of claim 1, wherein the first and second locking elements are biased in an extended position in which the first and second locking element is engaged with the respective mating element to hold the transducer in place, and wherein the locking assembly further includes one or more actuators that are configured to operate to move the first and second locking elements to a retracted position to disengage the respective first and second locking elements from the respective mating element.

5. The ultrasonic treatment device of claim 1, wherein the grooves or ridges are parallel to one another.

6. The ultrasonic treatment device of claim 5, wherein the grooves or ridges extend at least 75% of a circumference of the inner surface.

7. The ultrasonic treatment device of claim 1, wherein the locking assembly includes a screw to couple the locking assembly to the ultrasonic transducer such that the locking assembly is rotationally movable with respect to the ultrasonic transducer.

8. The ultrasonic treatment device of claim 7, wherein the screw includes a material that is visible in magnetic resonance imaging (MRI).

9. The ultrasonic treatment device of claim 1, further comprising the transducer.

10. The ultrasonic treatment device of claim 9, wherein the transducer includes one or more portions of a material that is visible in MRI.

11. The ultrasonic treatment device of claim 9, further comprising an acoustic pad that includes a rim embedded into the acoustic pad to engage the acoustic pad with a bottom portion of the transducer.

12. A transducer holder for an ultrasonic transducer, the transducer holder comprising:
    a circular body having an inner surface that is cylindrical; and
    a plurality of grooves that extend around the inner surface at different heights from a bottom plane of the transducer holder, wherein the grooves do not connect with one another, and wherein individual grooves of the plurality of grooves are adapted to engage with a first locking element and a second locking element of the ultrasonic transducer to hold the transducer at a selected one of multiple predefined, non-continuous mounting angles with respect to the transducer holder, wherein the plurality of grooves include at least a first groove, a second groove, and a third groove, and wherein the plurality of grooves are to:
    hold the ultrasonic transducer at a first predefined angle when the first and second locking elements are both engaged with the first groove;
    hold the ultrasonic transducer at a second predefined angle when the first locking element is engaged with the first groove and the second locking element is engaged with the second groove; and
    hold the ultrasonic transducer at a third predefined angle when the first locking element is engaged with the first groove and the second locking element is engaged with the third groove.

13. The transducer holder of claim 12, wherein the plurality of grooves are parallel to one another.

14. The transducer holder of claim 12, further comprising:
    a plurality of flanges extending outward from the circular body, wherein the plurality of flanges are adapted to be attached to one or more straps to secure the transducer holder to a patient, wherein at least one of the plurality of flanges is positioned above a bottom plane of the transducer holder.

15. The transducer holder of claim 12, further comprising a bottom surface that extends above the bottom plane at one or more portions to leave an opening between a patient and the one or more portions.

16. A system for ultrasonic treatment, the system comprising:
a transducer holder including:
a circular body having an inner surface that is cylindrical; and
a plurality of mating elements that extend around the inner surface at different heights from a bottom of the transducer holder, wherein the plurality of mating elements includes three or more mating elements including at least a first mating element, a second mating element, and a third mating element, and wherein the mating elements include respective grooves or ridges that do not connect with one another;
an ultrasonic transducer to generate an ultrasonic beam; and
a locking assembly that is rotatably attached to a top of the ultrasonic transducer to enable rotation of the locking assembly with respect to the ultrasonic transducer, wherein the locking assembly includes a first locking element and a second locking element that are each adapted to engage with any of the plurality of mating elements to hold the ultrasonic transducer at a selected angle with respect to the transducer holder, wherein the selected angle is selected from a plurality of predefined, non-continuous angles enabled by the plurality of mating elements, wherein the locking assembly is to:
hold the ultrasonic transducer at a first angle of 0 degrees when the first and second locking elements are both engaged with the first mating element;
hold the ultrasonic transducer at a second angle when the first locking element is engaged with the first mating element and the second locking element is engaged with the second mating element; and
hold the ultrasonic transducer at a third angle when the first locking element is engaged with the first mating element and the second locking element is engaged with the third mating element, wherein the second and third angles are non-zero and the third angle is greater than the second angle.

17. The system of claim 16, wherein the grooves or ridges are parallel to one another.

18. The system of claim 16, wherein the first and second locking elements are biased in an extended position in which the first and second locking element is engaged with the respective mating element to hold the transducer in place, and wherein the locking assembly further includes one or more actuators that are configured to operate to move the first and second locking elements to a retracted position to disengage the respective first and second locking elements from the respective mating element.

19. The system of claim 16, further comprising an acoustic pad that includes a rim embedded into the acoustic pad to engage the acoustic pad with a bottom portion of the transducer.

* * * * *